(12) United States Patent
Zeidler et al.

(10) Patent No.: US 9,359,446 B2
(45) Date of Patent: Jun. 7, 2016

(54) ANTIBODY TO A CARBONIC ANHYDRASE

(75) Inventors: Reinhard Zeidler, Olching (DE);
Christina Battke, Unterhaching (DE);
Elisabeth Kremmer, Freising (DE);
Andrew Flatley, Wessling (DE);
Claudiu Supuran, Florence (IT)

(73) Assignee: Hemholtz Zentrum Munchen—Deutches Forschungszentrum Fur Gesundheit Und Umwelt (GmbH), Neuherberg (DE)

( * ) Notice: Subject to any disclaimer, the term of this patent is extended or adjusted under 35 U.S.C. 154(b) by 483 days.

(21) Appl. No.: 13/696,011

(22) PCT Filed: May 2, 2011

(86) PCT No.: PCT/EP2011/056964
§ 371 (c)(1),
(2), (4) Date: Feb. 11, 2013

(87) PCT Pub. No.: WO2011/138279
PCT Pub. Date: Nov. 10, 2011

(65) Prior Publication Data
US 2013/0231465 A1 Sep. 5, 2013

(30) Foreign Application Priority Data
May 3, 2010 (EP) .................................. 10004646

(51) Int. Cl.
*A61K 39/395* (2006.01)
*C07K 16/40* (2006.01)
*C07K 16/30* (2006.01)

(52) U.S. Cl.
CPC ............. *C07K 16/40* (2013.01); *A61K 39/3955* (2013.01); *A61K 39/39558* (2013.01); *C07K 16/30* (2013.01)

(58) Field of Classification Search
None
See application file for complete search history.

(56) References Cited

U.S. PATENT DOCUMENTS

| 5,633,425 | A | * | 5/1997 | Lonberg et al. | .................. | 800/18 |
| 5,827,690 | A | * | 10/1998 | Meade et al. | .................... | 800/7 |
| 8,071,097 | B2 | * | 12/2011 | Wu et al. | .................... | 424/144.1 |

FOREIGN PATENT DOCUMENTS

CN          1167919       12/1997

OTHER PUBLICATIONS

Janeway et al., Immunobiology, 3rd edition, 1997, Garland Press, pp. 3:1-3:11.*
Rudikoff et al., Proc Natl Acad Sci USA, 1982, 79:1979-1983.*
Albers et al., Molecular Biology of the Cell, 3$^{rd}$ edition, 1994, Garland Publishing, pp. 56 and 57.*
Khairallah et al., Int Ophthalmol. Oct. 2010;30(5):465-83. doi: 10.1007/s10792-009-9319-6. Epub Aug. 27, 2009.*
Mandelcorn, E.D., Can J Ophthalmol. Feb. 2013;48(1):31-9. doi: 10.1016/j.jcjo.2012.11.013.*
Supuran: "Carbonic anhydrases: novel therapeutic applications for inhibitors and activators," Nature Reviews, Drug Discovery, Nature Publishing Group, vol. 7, Feb. 2008, pp. 168-181.
Pastorekova, et al.: "Cancer-Associated Carbonic Ahhydrases and Their Inhibition," Current Pharmaceutical Design, vol. 14, No. 7, Mar. 2008, pp. 685-698.
Parkkila et al.: "Carbonic anhydrase inhibitor suppresses invasion of renal cancer cells in vitro," PNAS, vol. 97, No. 5, Feb. 29, 2000, pp. 2220-2224.
Lam, et al.: "G250: A Carbonic Anhydrase IX Monoclonal Antibody," Current Oncology Reports, Current Science, vol. 7, No. 2, Feb. 16, 2010, pp. 109-115.
Tureci, et al.: "Human carbonic anhydrase XII: cDNA cloning, expression, and chromosomal localization of a carbonic anhydrase gene that is overexpressed in some renal cell cancers," Proc. Natl. Acad. Sci. USA, Jun. 1998, vol. 95, pp. 7608-7613.
Chiche, et al.: "Membrane-bound carbonic anhydrases are key pH regulators controlling tumor growth and cell migration," Advances in Enzyme Regulation, 2010, vol. 50, pp. 20-33.
Thiry, et al.: "Targeting tumor-associated carbonic anhydrase IX in cancer therapy," Trends in Pharmacological Sciences, Nov. 1, 2006, vol. 27, No. 11, pp. 566-573.
R&D Systems, Inc.: "Monoclonal Anti-human Carbonic Anhydrase XII Antibody," Apr. 13, 2007.
International Search Report for PCT/EP2011/056964.
Chiche et al.; Hypoxia-Inducible Carbonic Anhydrase IX and XII Promote Tumor Cell Growth by Counteracting Acidosis through the Regulation of the Intracellular pH; Cancer Res 2009, 69:(1) Jan. 1, 2009, pp. 358-368.
Chien et al.; Tumor-associated carbonic anhydrase XII is linked to the growth of primary oral squamous cell carcinoma and its poor prognosis; Oral Oncology 48 (2012), pp. 417-423.
Doyen et al.; Knock-down of hypoxia-induced carbonic anhydrases IX and XII radiosensitizes tumor cells by increasing ntracellular acidosis; Frontiers in Oncology, vol. 2, Article 199, Jan. 2013, pp. 1-10.

(Continued)

*Primary Examiner* — Michael Szperka
(74) *Attorney, Agent, or Firm* — Briggs and Morgan, P.A.; Audrey J. Babcock

(57) ABSTRACT

The present invention relates to an antibody binding to a carbonic anhydrase, wherein the antibody comprises (a) the amino acid sequences SEQ ID NOS. 1 (CDR 1), 2 (CDR 2) and 3 (CDR 3) determining the CDRs of the $V_H$ region, and the amino acid sequences SEQ ID NOS. 4 (CDR 1), 5 (CDR 2) and 6 (CDR 3) determining the CDRs of the $V_L$ region; or (b) the amino acids sequences of (a), wherein at least one amino acid is conservatively substituted in any one of the amino acid sequences SEQ ID NOS. 1 to 6.

18 Claims, 16 Drawing Sheets

(56) References Cited

OTHER PUBLICATIONS

Figure 1:
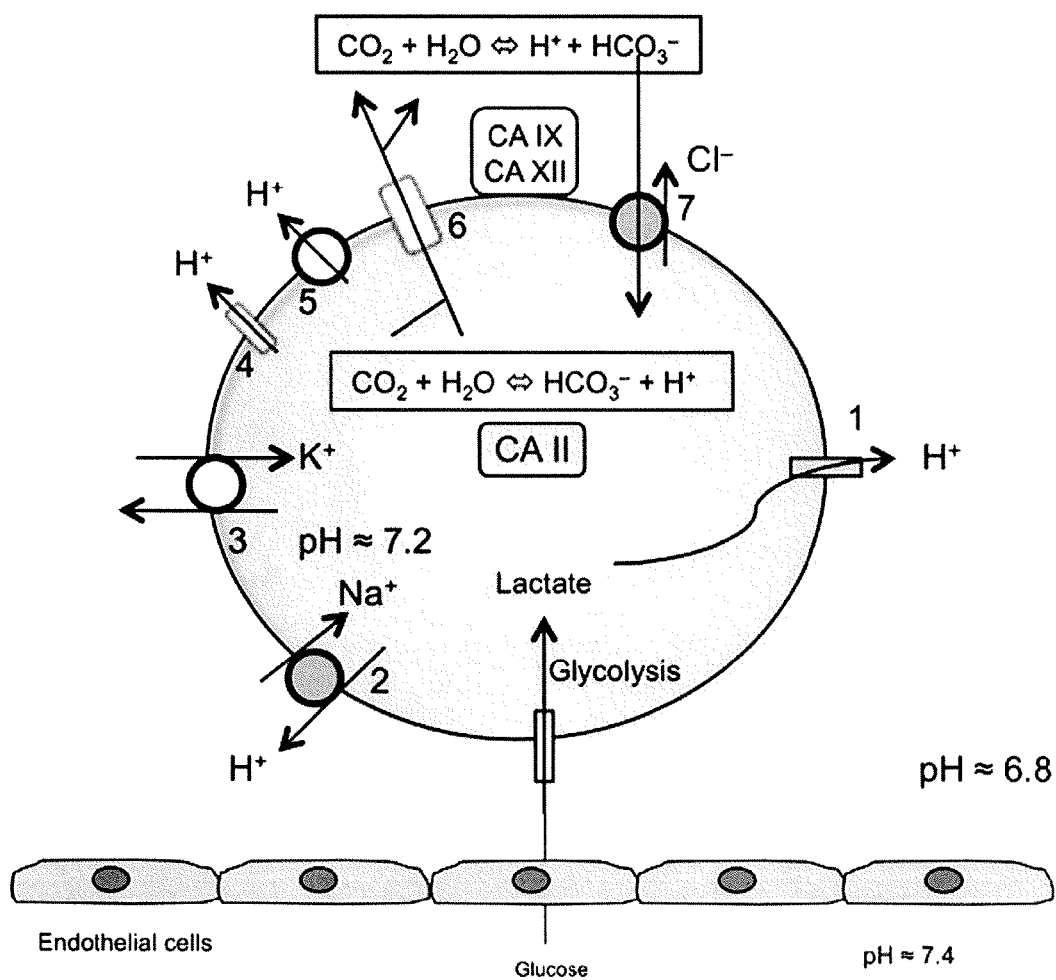

Karhumaa et al.; Identification of carbonic anhydrase XII as the membrane isozyme expressed in the normal human endometrial epithelium; Molecular Human Reproduction, vol. 6, No. 1, 2000, pp. 68-74.

Liu et al.; Gene Expression Profile in Human Trabecular Meshwork From Patients With Primary Open-Angle Glaucoma; IOVS, Sep. 2013, vol. 54, No. 9, pp. 6382-6389.

Lounnas et al.; Pharmacological inhibition of carbonic anhydrase XII interferes with cell proliferation and induces cell apoptosis on T-cell lymphomas; Cancer Letters 333, 2013, pp. 76-88.

Morris et al.; Targeting Hypoxic Tumor Cell Viability with Carbohydrate-Based Carbonic Anhydrase IX and XII nhibitors; J. Med. Chem. 2011, 54, Aug. 18, 2011, pp. 6905-6918.

Vullo et al.; Carbonic anhydrase inhibitors. Inhibition of the transmembrane isozyme XII with sulfonamides—a new target for the design of antitumor and antiglaucoma drugs?; Bioorg. Med. Chem. Lett. 15, 2005, pp. 963-969.

* cited by examiner

A

FIG. 4A (continued)
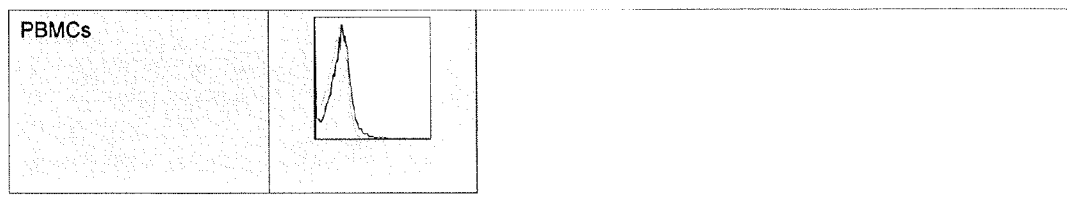
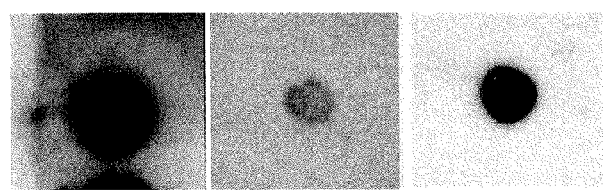
B      GM1    Iso    6A10

FIG. 5
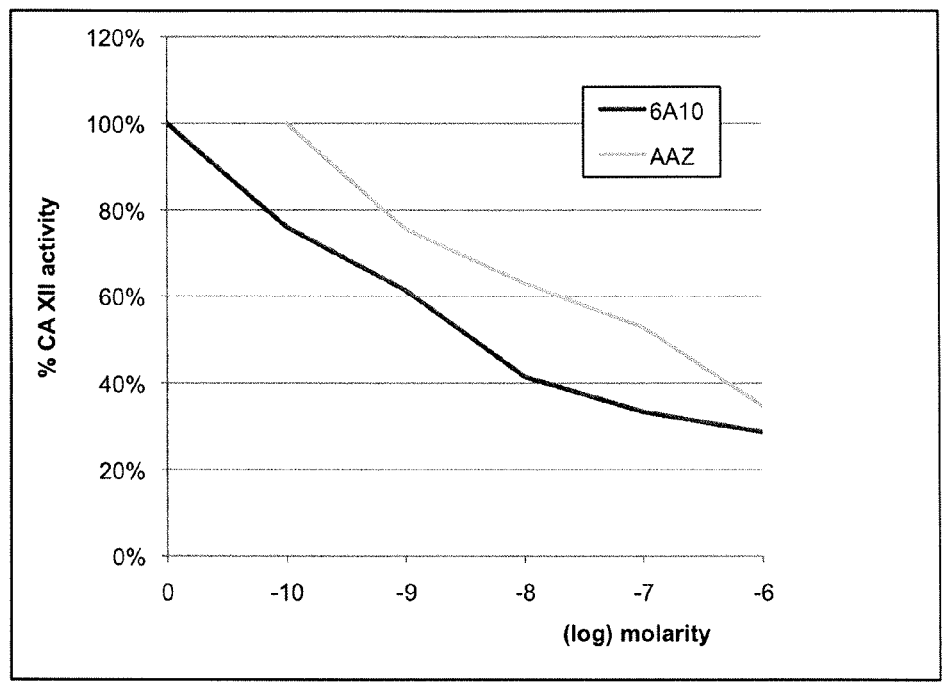
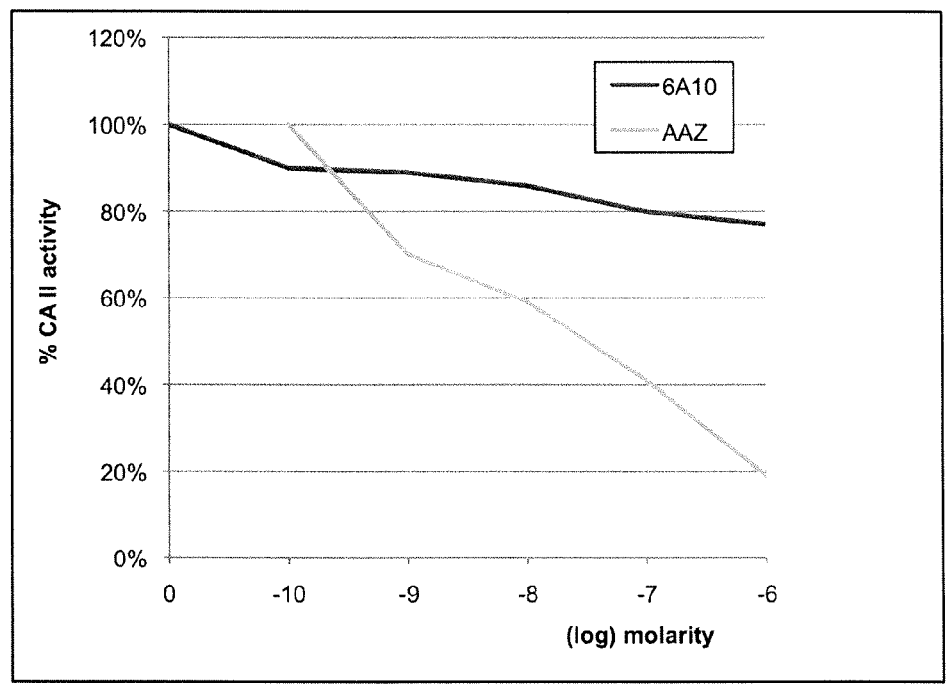

Note: "unbehandelt" = "untreated."

FIG. 8

```
ATG GCT CGA GTT TTT CAG CAA GAT GAT ATT GTG ATG ACC CAG ACT CCA
TAC CGA GCT CAA AAA GTC GTT CTA CTA TAA CAC TAC TGG GTC TGA GGT
 M   A   R   V   F   Q   Q   D   D   I   V   M   T   Q   T   P>

GCC ACC CTG TCT GTG ACT CCA GGA GAG AGT GTC AGT CTC TCC TGC AGG
CGG TGG GAC AGA CAC TGA GGT CCT CTC TCA CAG TCA GAG AGG ACG TCC
 A   T   L   S   V   T   P   G   E   S   V   S   L   S   C   R>

GCC AGT CAG GGT ATT AGC ACT AGC ATA CAC TGG TAT CAG CAA AAA TCA
CGG TCA GTC CCA TAA TCG TGA TCG TAT GTG ACC ATA GTC GTT TTT AGT
 A   S   Q   G   I   S   T   S   I   H   W   Y   Q   Q   K   S>

AAT GAG TCT CCA AGG CTT CTC ATC AAA TTT GCT TCC CAG TCC ATC TCT
TTA CTC AGA GGT TCC GAA GAG TAG TTT AAA CGA AGG GTC AGG TAG AGA
 N   E   S   P   R   L   L   I   K   F   A   S   Q   S   I   S>

GGA ATC CCC TCC AGG TTC AGT GGC AGT GGA TCA GGG ACA GAT TTC ACT
CCT TAG GGG AGG TCC AAG TCA CCG TCA CCT AGT CCC TGT CTA AAG TGA
 G   I   P   S   R   F   S   G   S   G   S   G   T   D   F   T>

CTC AGT ATC AAC AGA GTA GAA TCT GAA GAT TTT TCA GTT TAT TTC TGT
GAG TCA TAG TTG TCT CAT CTT AGA CTT CTA AAA AGT CAA ATA AAG ACA
 L   S   I   N   R   V   E   S   E   D   F   S   V   Y   F   C>

CAA CAG ACT TAC AGC TTG CCC TAC ACG TTT GGA GCT GGG ACC AAG CTG
GTT GTC TGA ATG TCG AAC GGG ATG TGC AAA CCT CGA CCC TGG TTC GAC
 Q   Q   T   Y   S   L   P   Y   T   F   G   A   G   T   K   L>

GAA CTG AAA CGG GCT GAT GGC TGC ACC AAC TGT ATC CAT CTT TCT AGA
CTT GAC TTT GCC CGA CTA CCG ACG TGG TTG ACA TAG GTA GAA AGA TCT
 E   L   K   R   A   D   G   C   T   N   C   I   H   L   S   R>

AGA TCT CCT ACA ATA TTC TCA GCT GCC ATG GAA AAT CGA TGT TCT TCT
TCT AGA GGA TGT TAT AAG AGT CGA CGG TAC CTT TTA GCT ACA AGA AGA
 R   S   P   T   I   F   S   A   A   M   E   N   R   C   S   S>

TTT ATT CTC TCA AGA TTT TCA GGC TGT ATA TTA AAA CTT ATA TTA AGA
```

FIG. 8 (continued)

```
AAA TAA GAG AGT TCT AAA AGT CCG ACA TAT AAT TTT GAA TAT AAT TCT
 F   I   L   S   R   F   S   G   C   I   L   K   L   I   L   R>

ACT ATG CTA ACC ACC TCA TCA GGA ACC GTT GTA GGT GGC
TGA TAC GAT TGG TGG AGT AGT CCT TGG CAA CAT CCA CCG
 T   M   L   T   T   S   S   G   T   V   V   G   G>
```

FIG. 9

```
GAG GTA AAG CTG GAG GAG TCA GGA CCT GGT CTG GTG CAG CCC TCA GAG
CTC CAT TTC GAC CTC CTC AGT CCT GGA CCA GAC CAC GTC GGG AGT CTC
 E   V   K   L   E   E   S   G   P   G   L   V   Q   P   S   E>

ACC CTG TCC CTC ACC TGC ACT GTC TCT GGG TTC TCA CTA ACC ACC TAT
TGG GAC AGG GAG TGG ACG TGA CAG AGA CCC AAG AGT GAT TGG TGG ATA
 T   L   S   L   T   C   T   V   S   G   F   S   L   T   T   Y>

AGT GTA AGT TGG GTT CGC CAG CCT TCA GGA AAA GGT CCT GAG TGG ATG
TCA CAT TCA ACC CAA GCG GTC GGA AGT CCT TTT CCA GGA CTC ACC TAC
 S   V   S   W   V   R   Q   P   S   G   K   G   P   E   W   M>

GGA AGA ATG TGG TAT GAT GGA GAC ACA GTG TAT AAT TCA GCT CTC AAA
CCT TCT TAC ACC ATA CTA CCT CTG TGT CAC ATA TTA AGT CGA GAG TTT
 G   R   M   W   Y   D   G   D   T   V   Y   N   S   A   L   K>

TCC CGA CTG AGC ATC AGC AGG GAC ACC TCC AAG AAC CAA GTT TTC TTA
AGG GCT GAC TCG TAG TCG TCC CTG TGG AGG TTC TTG GTT CAA AAG AAT
 S   R   L   S   I   S   R   D   T   S   K   N   Q   V   F   L>

AAA ATG AAC AGT CTG GAA ACT GAT GAA ACA GGC ACT TAC TAC TGT ACC
TTT TAC TTG TCA GAC CTT TGA CTA CTT TGT CCG TGA ATG ATG ACA TGG
 K   M   N   S   L   E   T   D   E   T   G   T   Y   Y   C   T>

AGA GAT TTC GGA TAC TTT GAT GGT AGT TCC CCC TTT GAT TAC TGG GGC
TCT CTA AAG CCT ATG AAA CTA CCA TCA AGG GGG AAA CTA ATG ACC CCG
 R   D   F   G   Y   F   D   G   S   S   P   F   D   Y   W   G>

CAA GGA GTC ATG GTC ACA GTC TCC TCA GCT GAA ACA ACA GCC CCA TCT
GTT CCT CAG TAC CAG TGT CAG AGG AGT CGA CTT TGT TGT CGG GGT AGA
 Q   G   V   M   V   T   V   S   S   A   E   T   T   A   P   S>

GTC TAT CCA CTG GCT CCT GGA ACT GCT CTC AAA AGT AAC TCC ATG GTG
CAG ATA GGT GAC CGA GGA CCT TGA CGA GAG TTT TCA TTG AGG TAC CAC
 V   Y   P   L   A   P   G   T   A   L   K   S   N   S   M   V>

ACC CTG GGA TGC CTG GTC AAG ATC TTG CTG AAA AAC TCG AGC CAT CCG
```

FIG. 9 (continued)

```
TGG GAC CCT ACG GAC CAG TTC TAG AAC GAC TTT TTG AGC TCG GTA GGC
 T   L   G   C   L   V   K   I   L   L   K   N   S   S   H   P>

GAA GAT CTG GCG GCC GCT CTC CCT ATA GTG AGT CGT ATT ACG CCG GAT
CTT CTA GAC CGC CGG CGA GAG GGA TAT CAC TCA GCA TAA TGC GGC CTA
 E   D   L   A   A   A   L   P   I   V   S   R   I   T   P   D>

GGA TAT GGT GTT CAG GCA CAA GTG TTA AAG CAG TTG ATT TTA TTC ACT
CCT ATA CCA CAA GTC CGT GTT CAC AAT TTC GTC AAC TAA AAT AAG TGA
 G   Y   G   V   Q   A   Q   V   L   K   Q   L   I   L   F   T>

ATG AGA AAA AAA CAA T
TAC TCT TTT TTT GTT A
 M   R   K   K   Q>
```

FIG. 11

MPRRSLHAAAVLLLVILKEQPSSPAPVNGSKWTYFGPDGENSWSKKYPSCGGLLQSPIDLHSDILQYDA
SLTPLEFQGYNLSANKQFLLTNNGHSVKLNLPSDMHIQGLQSRYSATQLHLWGNPNDPHGSEHTVSG
QHFAAELHIVHYNSDLYPDASTASNKSEGLAVLAVLIEMGSFNPSYDKIFSHLQHVKYKGQEAFVPGFNI
EELLPERTAEYYRYRGSLTTPPCNPTVLWTVFRNPVQISQEQLLALETALYCTHMDDPSPREMINNFRQ
VQKFDERLVYTSFSQVQVCTAAGLSLGIILSLALAGILGICIVVVVSIWLFRRKSIKKGDNKGVIYKPATKM
ETEAHA*

(Accession-No. NM_001218)
MPRRSLHAAAVLLLVILKEQPSSPAPVNGSKWTYFGPDGENSWSKKYPSCGGLLQSPIDLHSDILQYDA
SLTPLEFQGYNLSANKQFLLTNNGHSVKLNLPSDMHIQGLQSRYSATQLHLWGNPNDPHGSEHTVSG
QHFAAELHIVHYNSDLYPDASTASNKSEGLAVLAVLIEMGSFNPSYDKIFSHLQHVKYKGQEAFVPGFNI
EELLPERTAEYYRYRGSLTTPPCNPTVLWTVFRNPVQISQEQLLALETALYCTHMDDPSPREMINNFRQ
VQKFDERLVYTSFSQVQVCTAAGLSLGIILSLALAGILGICIVVVVSIWLFRRKSIKKGDNKGVIYKPATKM
ETEAHA

FIG. 12

ATGCCCCGGCGCAGCCTGCACGCGGCGGCCGTGCTCCTGCTGGTGATCTTAAAGGAACAGCCTT
CCAGCCCGGCCCCAGTGAACGGTTCCAAGTGGACTTATTTTGGTCCTGATGGGGAGAATAGCTGG
TCCAAGAAGTACCCGTCGTGTGGGGGCCTGCTGCAGTCCCCCATAGACCTGCACAGTGACATCCT
CCAGTATGACGCCAGCCTCACGCCCCTCGAGTTCCAAGGCTACAATCTGTCTGCCAACAAGCAGTT
TCTCCTGACCAACAATGGCCATTCAGTGAAGCTGAACCTGCCCTCGGACATGCACATCCAGGGCCT
CCAGTCTCGCTACAGTGCCACGCAGCTGCACCTGCACTGGGGGAACCCGAATGACCCGCACGGC
TCTGAGCACACCGTCAGCGGACAGCACTTCGCCGCCGAGCTGCACATTGTCCATTATAACTCAGAC
CTTTATCCTGACGCCAGCACTGCCAGCAACAAGTCAGAAGGCCTCGCTGTCCTGGCTGTTCTCATT
GAGATGGGCTCCTTCAATCCGTCCTATGACAAGATCTTCAGTCACCTTCAACATGTAAAGTACAAAG
GCCAGGAAGCATTCGTCCCGGGATTCAACATTGAAGAGCTGCTTCCGGAGAGGACCGCTGAATAT
TACCGCTACCGGGGGTCCCTGACCACACCCCCTTGCAACCCCACTGTGCTCTGGACAGTTTTCCG
AAACCCCGTGCAAATTTCCCAGGAGCAGCTGCTGGCTTTGGAGACAGCCCTGTACTGCACACACAT
GGACGACCCTTCCCCCAGAGAAATGATCAACAACTTCCGGCAGGTCCAGAAGTTCGATGAGAGGC
TGGTATACACCTCCTTCTCCCAAGTGCAAGTCTGTACTGCGGCAGGACTGAGTCTGGGCATCATCC
TCTCACTGGCCCTGGCTGGCATTCTTGGCATCTGTATTGTGGTGGTGGTGTCCATTTGGCTTTTCA
GAAGGAAGAGTATCAAAAAAGGTGATAACAAGGGAGTCATTTACAAGCCAGCCACCAAGATGGAGA
CTGAGGCCCACGCTTGA (Accession-No. NM_001218)
ATGCCCCGGCGCAGCCTGCACGCGGCGGCCGTGCTCCTGCTGGTGATCTTAAAGGAACAGCCTT
CCAGCCCGGCCCCAGTGAACGGTTCCAAGTGGACTTATTTTGGTCCTGATGGGGAGAATAGCTGG
TCCAAGAAGTACCCGTCGTGTGGGGGCCTGCTGCAGTCCCCCATAGACCTGCACAGTGACATCCT
CCAGTATGACGCCAGCCTCACGCCCCTCGAGTTCCAAGGCTACAATCTGTCTGCCAACAAGCAGTT
TCTCCTGACCAACAATGGCCATTCAGTGAAGCTGAACCTGCCCTCGGACATGCACATCCAGGGCCT
CCAGTCTCGCTACAGTGCCACGCAGCTGCACCTGCACTGGGGGAACCCGAATGACCCGCACGGC
TCTGAGCACACCGTCAGCGGACAGCACTTCGCCGCCGAGCTGCACATTGTCCATTATAACTCAGAC
CTTTATCCTGACGCCAGCACTGCCAGCAACAAGTCAGAAGGCCTCGCTGTCCTGGCTGTTCTCATT
GAGATGGGCTCCTTCAATCCGTCCTATGACAAGATCTTCAGTCACCTTCAACATGTAAAGTACAAAG
GCCAGGAAGCATTCGTCCCGGGATTCAACATTGAAGAGCTGCTTCCGGAGAGGACCGCTGAATAT
TACCGCTACCGGGGGTCCCTGACCACACCCCCTTGCAACCCCACTGTGCTCTGGACAGTTTTCCG
AAACCCCGTGCAAATTTCCCAGGAGCAGCTGCTGGCTTTGGAGACAGCCCTGTACTGCACACACAT
GGACGACCCTTCCCCCAGAGAAATGATCAACAACTTCCGGCAGGTCCAGAAGTTCGATGAGAGGC
TGGTATACACCTCCTTCTCCCAAGTGCAAGTCTGTACTGCGGCAGGACTGAGTCTGGGCATCATCC
TCTCACTGGCCCTGGCTGGCATTCTTGGCATCTGTATTGTGGTGGTGGTGTCCATTTGGCTTTTCA
GAAGGAAGAGTATCAAAAAAGGTGATAACAAGGGAGTCATTTACAAGCCAGCCACCAAGATGGAGA
CTGAGGCCCACGCTTGA ated on May 3, 2010, having 11.3 Kb (kilobytes) of data, and filed

SEQUENCE LISTING

```
<160> NUMBER OF SEQ ID NOS: 18

<210> SEQ ID NO 1
<211> LENGTH: 11
<212> TYPE: PRT
<213> ORGANISM: Rattus norvegicus

<400> SEQUENCE: 1

Arg Ala Ser Gln Gly Ile Ser Thr Ser Ile His
1               5                   10

<210> SEQ ID NO 2
<211> LENGTH: 7
<212> TYPE: PRT
<213> ORGANISM: Rattus norvegicus
```

<400> SEQUENCE: 2

Phe Ala Ser Gln Ser Ile Ser
1               5

<210> SEQ ID NO 3
<211> LENGTH: 10
<212> TYPE: PRT
<213> ORGANISM: Rattus norvegicus

<400> SEQUENCE: 3

Gln Gln Thr Tyr Ser Leu Pro Tyr Thr Phe
1               5                  10

<210> SEQ ID NO 4
<211> LENGTH: 10
<212> TYPE: PRT
<213> ORGANISM: Rattus norvegicus

<400> SEQUENCE: 4

Gly Phe Ser Leu Thr Thr Tyr Ser Val Ser
1               5                  10

<210> SEQ ID NO 5
<211> LENGTH: 9
<212> TYPE: PRT
<213> ORGANISM: Rattus norvegicus

<400> SEQUENCE: 5

Arg Met Trp Tyr Asp Gly Asp Thr Val
1               5

<210> SEQ ID NO 6
<211> LENGTH: 13
<212> TYPE: PRT
<213> ORGANISM: Rattus norvegicus

<400> SEQUENCE: 6

Asp Phe Gly Tyr Phe Asp Gly Ser Ser Pro Phe Asp Tyr
1               5                  10

<210> SEQ ID NO 7
<211> LENGTH: 173
<212> TYPE: PRT
<213> ORGANISM: Rattus norvegicus

<400> SEQUENCE: 7

Met Ala Arg Val Phe Gln Gln Asp Asp Ile Val Met Thr Gln Thr Pro
1               5                  10                  15

Ala Thr Leu Ser Val Thr Pro Gly Glu Ser Val Ser Leu Ser Cys Arg
            20                  25                  30

Ala Ser Gln Gly Ile Ser Thr Ser Ile His Trp Tyr Gln Gln Lys Ser
        35                  40                  45

Asn Glu Ser Pro Arg Leu Leu Ile Lys Phe Ala Ser Gln Ser Ile Ser
    50                  55                  60

Gly Ile Pro Ser Arg Phe Ser Gly Ser Gly Ser Gly Thr Asp Phe Thr
65                  70                  75                  80

Leu Ser Ile Asn Arg Val Glu Ser Glu Asp Phe Ser Val Tyr Phe Cys
                85                  90                  95

Gln Gln Thr Tyr Ser Leu Pro Tyr Thr Phe Gly Ala Gly Thr Lys Leu
            100                 105                 110

Glu Leu Lys Arg Ala Asp Gly Cys Thr Asn Cys Ile His Leu Ser Arg
            115                 120                 125

Arg Ser Pro Thr Ile Phe Ser Ala Ala Met Glu Asn Arg Cys Ser Ser
        130                 135                 140

Phe Ile Leu Ser Arg Phe Ser Gly Cys Ile Leu Lys Leu Ile Leu Arg
145                 150                 155                 160

Thr Met Leu Thr Thr Ser Ser Gly Thr Val Val Gly Gly
                165                 170

<210> SEQ ID NO 8
<211> LENGTH: 197
<212> TYPE: PRT
<213> ORGANISM: Rattus norvegicus

<400> SEQUENCE: 8

Glu Val Lys Leu Glu Glu Ser Gly Pro Gly Leu Val Gln Pro Ser Glu
1               5                   10                  15

Thr Leu Ser Leu Thr Cys Thr Val Ser Gly Phe Ser Leu Thr Thr Tyr
            20                  25                  30

Ser Val Ser Trp Val Arg Gln Pro Ser Gly Lys Gly Pro Glu Trp Met
        35                  40                  45

Gly Arg Met Trp Tyr Asp Gly Asp Thr Val Tyr Asn Ser Ala Leu Lys
    50                  55                  60

Ser Arg Leu Ser Ile Ser Arg Asp Thr Ser Lys Asn Gln Val Phe Leu
65                  70                  75                  80

Lys Met Asn Ser Leu Glu Thr Asp Glu Thr Gly Thr Tyr Tyr Cys Thr
                85                  90                  95

Arg Asp Phe Gly Tyr Phe Asp Gly Ser Ser Pro Phe Asp Tyr Trp Gly
            100                 105                 110

Gln Gly Val Met Val Thr Val Ser Ser Ala Glu Thr Thr Ala Pro Ser
        115                 120                 125

Val Tyr Pro Leu Ala Pro Gly Thr Ala Leu Lys Ser Asn Ser Met Val
    130                 135                 140

Thr Leu Gly Cys Leu Val Lys Ile Leu Leu Lys Asn Ser Ser His Pro
145                 150                 155                 160

Glu Asp Leu Ala Ala Ala Leu Pro Ile Val Ser Arg Ile Thr Pro Asp
                165                 170                 175

Gly Tyr Gly Val Gln Ala Gln Val Leu Lys Gln Leu Ile Leu Phe Thr
            180                 185                 190

Met Arg Lys Lys Gln
        195

<210> SEQ ID NO 9
<211> LENGTH: 33
<212> TYPE: DNA
<213> ORGANISM: Rattus norvegicus

<400> SEQUENCE: 9
agggccagtc agggtattag cactagcata cac                                33

<210> SEQ ID NO 10
<211> LENGTH: 21
<212> TYPE: DNA
<213> ORGANISM: Rattus norvegicus

<400> SEQUENCE: 10
tttgcttccc agtccatctc t                                              21

```
<210> SEQ ID NO 11
<211> LENGTH: 30
<212> TYPE: DNA
<213> ORGANISM: Rattus norvegicus

<400> SEQUENCE: 11
caacagactt acagcttgcc ctacacgttt                                      30

<210> SEQ ID NO 12
<211> LENGTH: 519
<212> TYPE: DNA
<213> ORGANISM: Rattus norvegicus

<400> SEQUENCE: 12
atggctcgag tttttcagca agatgatatt gtgatgaccc agactccagc caccctgtct     60
gtgactccag gagagagtgt cagtctctcc tgcagggcca gtcagggtat tagcactagc    120
atacactggt atcagcaaaa atcaaatgag tctccaaggc ttctcatcaa atttgcttcc    180
cagtccatct ctggaatccc ctccaggttc agtggcagtg gatcagggac agatttcact    240
ctcagtatca acagagtaga atctgaagat ttttcagttt atttctgtca acagacttac    300
agcttgccct acacgtttgg agctgggacc aagctggaac tgaaacgggc tgatggctgc    360
accaactgta tccatctttc tagaagatct cctacaatat tctcagctgc catggaaaat    420
cgatgttctt cttttattct ctcaagattt tcaggctgta tattaaaact tatattaaga    480
actatgctaa ccacctcatc aggaaccgtt gtaggtggc                           519

<210> SEQ ID NO 13
<211> LENGTH: 30
<212> TYPE: DNA
<213> ORGANISM: Rattus norvegicus

<400> SEQUENCE: 13
gggttctcac taaccaccta tagtgtaagt                                      30

<210> SEQ ID NO 14
<211> LENGTH: 27
<212> TYPE: DNA
<213> ORGANISM: Rattus norvegicus

<400> SEQUENCE: 14
agaatgtggt atgatggaga cacagtg                                         27

<210> SEQ ID NO 15
<211> LENGTH: 39
<212> TYPE: DNA
<213> ORGANISM: Rattus norvegicus

<400> SEQUENCE: 15
gatttcggat actttgatgg tagttccccc tttgattac                            39

<210> SEQ ID NO 16
<211> LENGTH: 592
<212> TYPE: DNA
<213> ORGANISM: Rattus norvegicus

<400> SEQUENCE: 16
gaggtaaagc tggaggagtc aggacctggt ctggtgcagc cctcagagac cctgtccctc     60
acctgcactg tctctgggtt ctcactaacc acctatagtg taagttgggt tcgccagcct    120
tcaggaaaag gtcctgagtg gatgggaaga atgtggtatg atggagacac agtgtataat    180
```

```
tcagctctca aatcccgact gagcatcagc agggacacct ccaagaacca agttttctta    240
aaaatgaaca gtctggaaac tgatgaaaca ggcacttact actgtaccag agatttcgga    300
tactttgatg gtagttcccc ctttgattac tggggccaag gagtcatggt cacagtctcc    360
tcagctgaaa caacagcccc atctgtctat ccactggctc ctggaactgc tctcaaaagt    420
aactccatgg tgaccctggg atgcctggtc aagatcttgc tgaaaaactc gagccatccg    480
gaagatctgg cggccgctct ccctatagtg agtcgtatta cgccggatgg atatggtgtt    540
caggcacaag tgttaaagca gttgatttta ttcactatga gaaaaaaaca at            592
```

<210> SEQ ID NO 17  
<211> LENGTH: 354  
<212> TYPE: PRT  
<213> ORGANISM: Homo sapiens

<400> SEQUENCE: 17

```
Met Pro Arg Arg Ser Leu His Ala Ala Val Leu Leu Val Ile
1               5                   10                  15

Leu Lys Glu Gln Pro Ser Ser Pro Ala Pro Val Asn Gly Ser Lys Trp
                20                  25                  30

Thr Tyr Phe Gly Pro Asp Gly Glu Asn Ser Trp Ser Lys Lys Tyr Pro
            35                  40                  45

Ser Cys Gly Gly Leu Leu Gln Ser Pro Ile Asp Leu His Ser Asp Ile
        50                  55                  60

Leu Gln Tyr Asp Ala Ser Leu Thr Pro Leu Glu Phe Gln Gly Tyr Asn
65                  70                  75                  80

Leu Ser Ala Asn Lys Gln Phe Leu Leu Thr Asn Asn Gly His Ser Val
                85                  90                  95

Lys Leu Asn Leu Pro Ser Asp Met His Ile Gln Gly Leu Gln Ser Arg
            100                 105                 110

Tyr Ser Ala Thr Gln Leu His Leu His Trp Gly Asn Pro Asn Asp Pro
        115                 120                 125

His Gly Ser Glu His Thr Val Ser Gly Gln His Phe Ala Ala Glu Leu
    130                 135                 140

His Ile Val His Tyr Asn Ser Asp Leu Tyr Pro Asp Ala Ser Thr Ala
145                 150                 155                 160

Ser Asn Lys Ser Glu Gly Leu Ala Val Leu Ala Val Leu Ile Glu Met
                165                 170                 175

Gly Ser Phe Asn Pro Ser Tyr Asp Lys Ile Phe Ser His Leu Gln His
            180                 185                 190

Val Lys Tyr Lys Gly Gln Glu Ala Phe Val Pro Gly Phe Asn Ile Glu
        195                 200                 205

Glu Leu Leu Pro Glu Arg Thr Ala Glu Tyr Tyr Arg Tyr Arg Gly Ser
    210                 215                 220

Leu Thr Thr Pro Pro Cys Asn Pro Thr Val Leu Trp Thr Val Phe Arg
225                 230                 235                 240

Asn Pro Val Gln Ile Ser Gln Glu Gln Leu Leu Ala Leu Glu Thr Ala
                245                 250                 255

Leu Tyr Cys Thr His Met Asp Asp Pro Ser Pro Arg Glu Met Ile Asn
            260                 265                 270

Asn Phe Arg Gln Val Gln Lys Phe Asp Glu Arg Leu Val Tyr Thr Ser
        275                 280                 285

Phe Ser Gln Val Gln Val Cys Thr Ala Ala Gly Leu Ser Leu Gly Ile
    290                 295                 300
```

```
Ile Leu Ser Leu Ala Leu Ala Gly Ile Leu Gly Ile Cys Ile Val Val
305                 310                 315                 320

Val Val Ser Ile Trp Leu Phe Arg Arg Lys Ser Ile Lys Lys Gly Asp
                325                 330                 335

Asn Lys Gly Val Ile Tyr Lys Pro Ala Thr Lys Met Glu Thr Glu Ala
            340                 345                 350

His Ala

<210> SEQ ID NO 18
<211> LENGTH: 1065
<212> TYPE: DNA
<213> ORGANISM: Homo sapiens

<400> SEQUENCE: 18
atgccccggc gcagcctgca cgcggcggcc gtgctcctgc tggtgatctt aaaggaacag        60
ccttccagcc cggccccagt gaacggttcc aagtggactt attttggtcc tgatggggag       120
aatagctggt ccaagaagta cccgtcgtgt ggggcctgc tgcagtcccc catagacctg        180
cacagtgaca tcctccagta tgacgccagc ctcacgcccc tcgagttcca aggctacaat       240
ctgtctgcca acaagcagtt tctcctgacc aacaatggcc attcagtgaa gctgaacctg       300
ccctcggaca tgcacatcca gggcctccag tctcgctaca gtgccacgca gctgcacctg       360
cactggggga acccgaatga cccgcacggc tctgagcaca ccgtcagcgg acagcacttc       420
gccgccgagc tgcacattgt ccattataac tcagaccttt atcctgacgc agcactgcc        480 agcaacaagt cagaaggcct cgctgtcctg gctgttctca ttgagatggg ctccttcaat       540
ccgtcctatg acaagatctt cagtcacctt aacatgtaa agtacaaagg ccaggaagca        600
ttcgtcccgg gattcaacat tgaagagctg cttccggaga ggaccgctga atattaccgc       660
taccgggggt ccctgaccac accccttgc aacccactg tgctctggac agttttccga        720
aaccccgtgc aaatttccca ggagcagctg ctggctttgg agacagccct gtactgcaca       780
cacatggacg acccttcccc cagagaaatg atcaacaact ccggcaggt ccagaagttc        840 gatgagaggc tggtatacac ctccttctcc caagtgcaag tctgtactgc ggcaggactg       900
agtctgggca tcatcctctc actggccctg gctggcattc ttggcatctg tattgtggtg       960
gtggtgtcca tttggctttt cagaaggaag agtatcaaaa aaggtgataa caagggagtc      1020
atttacaagc cagccaccaa gatggagact gaggcccacg cttga                      1065
```

ANTIBODY TO A CARBONIC ANHYDRASE

INCORPORATION BY REFERENCE OF SEQUENCE LISTING

The text file entitled "Sequence list as filed.TXT," created on May 3, 2010, having 11.3 Kb (kilobytes) of data, and filed concurrently herewith, is hereby incorporated by reference in its entirety in this application.

The present invention relates to an antibody binding to a carbonic anhydrase, wherein the antibody comprises (a) the amino acid sequences SEQ ID NOS. 1 (CDR 1), 2 (CDR 2) and 3 (CDR 3) determining the CDRs of the $V_H$ region, and/or the amino acid sequences SEQ ID NOS. 4 (CDR 1), 5 (CDR 2) and 6 (CDR 3) determining the CDRs of the $V_L$ region; or (b) the amino acids sequences of (a), wherein at least one amino acid is conservatively substituted in any one of the amino acid sequences SEQ ID NOS. 1 to 6.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Carbonic anhydrases are a family of enzymes that catalyze the reversible hydration of carbonic acid to bicarbonate and protons, and thus participate in the maintenance of pH homeostasis in the body (Badger and Price (1994), Annu. Rev. Plant Physiol. Plant Mol. Bio., 45:369-392). In the absence of a catalyst this reaction occurs rather slowly. Since most carbonic anhydrases contain a zinc ion in their active site they are classified as being metalloenzymes.

The familiy of carbonic anhydrases has serveral members. There are at least five distinct CA subfamilies ($\alpha$, $\beta$, $\gamma$, $\delta$ and $\epsilon$). These subfamilies have no significant amino acid sequence similarity and in most cases are thought to be an example of convergent evolution. The $\alpha$-carbonic anhydrases (CAs) are found in mammals. The members of this subfamiliy can be distinguished with respect to their kinetics, tissue expression and subcellular localization (Kivela et al 2005).

$\alpha$-CA enzymes are divided into four broad subgroups, namely into the cytosolic CAs (CA-I, CA-II, CA-III, CA-VII and CA-XIII), mitochondrial CAs (CA-VA and CA-VB), secreted CAs (CA-VI), and membrane-associated CAs (CA-IV, CA-IX, CA-XII, CA-XIV and CA-XV) (Breton et al. (2001), JOP 2(4 Suppl):159-64). Moreover, there are three "catalytic" CA isoforms (CA-VIII, CA-X, and CA-XI) whose functions remain unclear. Of all these CAs several isoforms exist in addition.

CA-II, CA-IX and CA-XII have been associated with neoplastic processes, and they are potential histological and prognostic biomarkers of various tumours (Nordfors et al. (2010), BMC cancer; 10:148). CA-II is the most widely expressed member of the $\alpha$-CA gene family, being present in virtually every human tissue and organ. It is catalytically one of the most efficient enzymes known. It is present to some extent in malignant cells, and, interestingly, it has been recently shown to be ectopically expressed in the endothelial cells of tumour neovessels. The transmembrane enzyme, CA-IX, was first recognised as a novel tumour-associated antigen expressed in several types of human carcinomas as well as in normal gastrointestinal tissue. CA-IX has been functionally linked to cell adhesion, differentiation, proliferation and oncogenic processes, and its enzymatic activity is comparable to CA II. Another transmembrane CA isozyme, CA-XII, was first found in normal kidney tissue and renal cell carcinoma. Further studies have shown that it is expressed in several other tumours (Ulmasov et al. (2000)), but also in some normal organs such as the colon and uterus. The X-ray crystallographic structure of human CA-XII reveals that it is a bitopic dimeric protein whose short intracellular C-terminus is placed on the opposite side of the active site domains such that the latter face is towards the extracellular space.

High expression of CA-II, CA-IX and CA-XII in tumours, particularly under hypoxic conditions has further suggested that these enzymes may functionally participate in the invasion process, which is facilitated by acidification of the extracellular space. In favour of this hypothesis, it has been shown in vitro that CA inhibitors can reduce the invasion capacity and proliferation of cancer cells (Manokaran et al. (2008), J Biomed Nanotechnol., 4(4):491-498). In particular, CA IX and XII seem to be regulated by similar mechanisms, as transcription of these isozymes is induced in tumours under hypoxic conditions through hypoxia inducible factor-1 alpha (HIF-1$\alpha$)-mediated pathways (Chiche et al. (2009)). In addition, it has been shown that the expression of CA-XII is highly correlated with estrogen receptor alpha (ER$\alpha$) in breast tumours (Barnett et al. (2008), Cancer Res 68:3505-3515). To explain the importance of CAs in cancer progression in more detail, the rapidly proliferating tumour cells quickly overgrow such that the diffusion of oxygen from the nearest blood vessel (100-150 µm) is impaired. Consequently, tumour cells receive low level of oxygen, causing local hypoxic centres and tissue necrosis. Hypoxia creates selective pressure in cells to adopt to stress conditions, resulting in the expression of approximately 50 additional proteins, including the enzymes involved in pH homeostasis (Potter et al. (2004), Cell Cycle, 3:164-167). As explained above, the latter is accomplished, at least in part, by an intricate coordination between selected carbonic anhydrase (CA) isozymes, particularly CA-II, CA-IX and CA-XII. A direct link between CA XII and cancer has been demonstrated by Proescholdt et al. (2005), Neuro Onco 7:465-475. Here it is demonstrated that CA XII expression is upregulated in intrinsic and metastatic brain tumours as compared to normal brain tissue. Furthermore, Ilie et al. (2011), In J Cancer, 128(7):1614-23 and Hynninen et al. (2006), Histopathology, 49:594-602 showed overexpression of CA XII in tissues from resectable non-small lung cancer and ovarian cancer, respectively. Hsieh et al. (2010), Eur J Cell Biol, 89:598-606 revealed in vivo and in vitro that CA XII is associated with invasion and metastasis of tumour cell lines.

Moreover, CA-inhibitors, in particular inhibitors of CA-II and CA-XII are used to reduce intraocular pressure and thus to treat ocular hypertension (Al-Barrag et al. (2009), Clinical Ophthalomology 3:357-362). Also, CA-inhibitors were shown to be useful in the treatment of glaucoma (Haapasalo et al. (2008), Neuro Oncology 3:357-362, and Vullo et al. 2005).

Accordingly, CAs, and in particular CA-XII, are known to play a role in hypoxia, cancer and eye diseases and are therefore important targets for a therapeutical treatment or diagnosis (Thiry et al 2008, Vulo et al 2005, and Haapasalo et al. (2008), Neuro Oncology 3:357-362). Although systemic carbonic anhydrase inhibitors are known in the art, they are associated with adverse side effects, such as acid-base disturbance, hypersensitivity reactions, and fatal aplasmatic anemia (Gross et al. (1988), Am J Opthamol., Naeser et al. (1986), Acta Opthalmol., 64:330-337, Mastropasqua et al. (1998), 212:318-321; and Passp et al, Br J Opthalmol. 1985; 69:572-575). Thus, further means and methods are required that may be employed in the development of further therapeutic and diagnostic means for the above mentioned diseases.

This need is addressed by the provision of the embodiments characterized in the claims. Accordingly the invention relates in first embodiment to an antibody binding to a carbonic anhydrase, wherein the antibody comprises (a) the amino acid sequences SEQ ID NOS. 1 (CDR 1), 2 (CDR 2) and 3 (CDR 3) determining the CDRs of the $V_H$ region, and/or the amino acid sequences SEQ ID NOS. 4 (CDR 1), 5 (CDR 2) and 6 (CDR 3) determining the CDRs of the $V_L$ region; or (b) the amino acids sequences of (a), wherein at least one amino acid is conservatively substituted in any one of the amino acid sequences SEQ ID NOS. 1 to 6.

Figure 6:
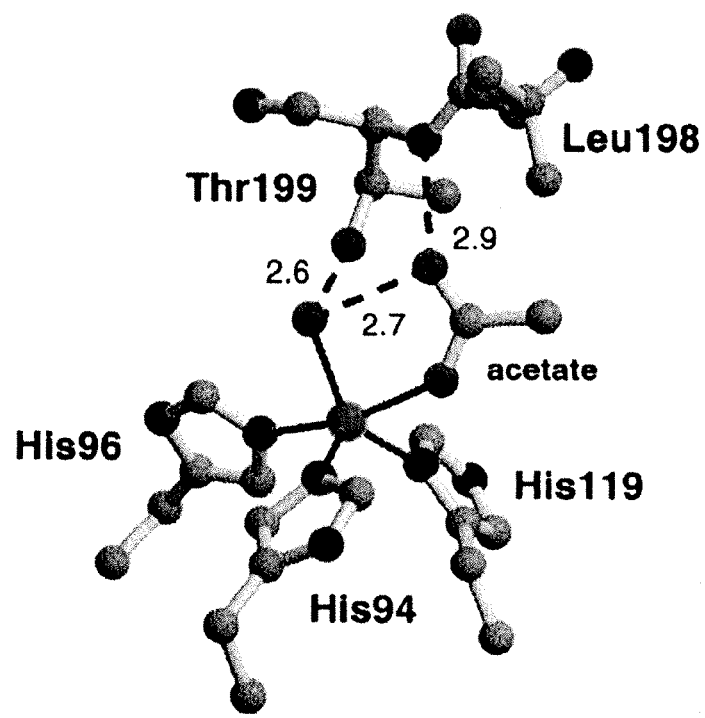

The term "antibody", in accordance with the present invention, comprises polyclonal and monoclonal antibodies as well as derivatives or fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" in accordance with the invention also includes embodiments such as chimeric, single chain and humanized antibodies, as well as antibody fragments, like, inter alia, Fab fragments, fusion proteins consisting of Eph receptors, ephrin or phosphatase extracellular domains and Fc. Antibody fragments or derivatives further comprise $F(ab')_2$, Fv fragments or scFvs; see, for example, Harlow and Lane (1988) and (1999), loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies specific for polypeptide(s) and fusion proteins of this invention. Also, transgenic animals may be used to express humanized antibodies specific for polypeptides and fusion proteins of this invention. Most preferably, the antibody of this invention is a monoclonal antibody. For the preparation of monoclonal antibodies, any technique, which provides antibodies produced by continuous cell line cultures, can be used. Examples for such techniques include the original hybridoma technique (Köhler and Milstein (1975) Nature 256, 495) as further developed by the art, the trioma technique, the human B-cell hybridoma technique (Kozbor (1983) Immunology Today 4, 72) and the EBV-hybridoma technique to produce human monoclonal antibodies (Cole et al. (1985) Monoclonal Antibodies and Cancer Therapy, Alan R. Liss, Inc., 77). Surface plasmon resonance as employed in the BIAcore system can be used to increase the efficiency of phage antibodies, which bind to an epitope of a polypeptide of the invention (Schier (1996) Human Antibodies Hybridomas 7, 97; Malmborg (1995) J. Immunol. Methods 183, 7). It is also envisaged in the context of this invention that the term "antibody" comprises antibody constructs, which may be expressed in cells, e.g. antibody constructs which may be transfected and/or transduced via, amongst others, viruses or plasmid vectors. The antibody described in the context of the invention is capable to specifically bind/interact with an epitope of the mentioned polypeptide, preferably CA-XII, CA-XII being as defined further herein. The term "specifically binding/interacting with" as used in accordance with the present invention means that the antibody does not or essentially does not cross-react with an epitope of similar structure. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of a CA, in particular CA-XII) but do not or do not essentially bind to any of the other epitope are considered specific for the epitope of interest and thus to be antibodies in accordance with this invention. Corresponding methods are described e.g. in Harlow and Lane, 1988 and 1999, loc cit. The antibody specifically binds to/interacts with conformational or continuous epitopes, which are unique for the mentioned polypeptide, preferably CA-XII. A conformational or discontinuous epitope is characterized for polypeptide antigens by the presence of two or more discrete amino acid residues which are separated in the primary sequence, but come together on the surface of the molecule when the polypeptide folds into the native protein/antigen (Sela (1969) Science 166, 1365; laver (1990) Cell 61, 553). The two or more discrete amino acid residues contributing to the epitope are present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues, which are present in a single linear segment of a polypeptide chain. Antibodies may be administered for example as described in WO/2000/029019 and U.S. Pat. No. 6,294,171. In this regard, it is mentioned that the catalytic domain of CA-XII whose catalytic activity is inhibited by the antibody EXO 6A10 is shown in FIG. 6.

The term "CDR" is well known in the state of the art and specifies the Complementarity Determining Region (see, for example, Harlow and Lane, "Antibodies, a laboratory manual", CSH Press, Cold Spring Harbour, 1988). A CDR is a relatively short amino acid sequence found in the variable (V) domains of an antibody. Each variable domain (the heavy chain $V_H$ and light chain $V_L$) of an antibody comprises three complementarity determining regions sometimes called hypervariable regions, flanked by four relatively conserved framework regions or "FRs". The six CDRs of an antibody essentially determine the specificity of an antibody and make the contact with a specific ligand.

The person skilled in the art will readily appreciate that the variable domain of the antibody, having the above-described CDRs (SEQ ID NOs 1 to 6) can be used for the construction of antibodies of further improved specificity and biological function. Insofar, the present invention encompasses antibodies comprising the above-described variable domains which advantageously have substantially the same, similar or improved binding properties as the antibody described in the appended examples.

According to the invention the antibodies of the present invention or their corresponding immunoglobulin chain(s) can therefore be further modified by at least one conservative amino acid substitution(s) in any one of the amino acid sequences SEQ ID NOS. 1 to 6. In this regard it is preferred with increasing preference that less than 10, less than 9, less than 8, less than 7, less than 6, less than 5, less than 4, less than 3, less than 2 amino acids are, or 1 amino acid is conservatively substituted in any one of the amino acid sequences SEQ ID NOS. 1 to 6.

The term "conservative substitution" is widely used in the state of the art and specifies the replacement of an amino acid in a polypeptide by an amino acid with similar characteristics. Similar characteristics are for example size, hydrophobicity, or charge. As it is well known, amino acids are classified as being positively charged, negatively charged, having an uncharged side chain or a hyrophobic side chain. Examples for a conservative substitution are Leu to Ile, Arg for Lys, Phe to Trp, Asp to Glu, Ser to Thr, or vice versa. In general, the overall functioning of a amino acid sequence in particular amino acid sequence of CDR is likely not to be essentially affected by conservative substitution and may even be improved.

Methods for introducing such modifications, in particular amino acid substitution(s) in the DNA sequence encoding the amino acid sequence of an CDR are well known to the person skilled in the art; see, e.g., Sambrook, Molecular Cloning A Laboratory Manual, Cold Spring Harbor Laboratory (1989) N.Y.

The antibody of the invention shows advantageous properties with respect to its inhibiting and biological activity. As can be seen from the appended examples the antibody EXO 6A10 comprising the CDRs having SEQ ID NOs 1 to 6, inhibits the enzyme activity of CA-XII 40-times better as compared to sulfonamid azedazolamide (i.e. a known inhibitor of CAs, e.g. from Kaur et al. (2002), Int J Pharm 248 (1-2): 1-14). Furthermore, the instant examples show that the antibody EXO 6A10 inhibits the growth of the tumour cell line A549 (derived from adenocarcinoma) under hypotoxic culture conditions.

To the best knowledge of the inventors, EXO 6A10 is thus the first antibody identified which inhibits the activity of CA-XII on living cells. This is a proof of concept of the suitability of the antibody provided by the invention for therapeutic and diagnostic means of a disease associated with carbonic anhydrase activity and in particular the activity of CA-XII.

The antibody of the invention is expected to bind to various members of the CAs, preferably the other membrane-associated a-carbonic anhydrases (CAs) whose extracellular active site cavities share homologies (Alterio et al. (2009) PNAS 106:16233-16238). It is more preferred that the antibody of the invention binds to the membrane-associated CAs CA-IX or CA-XII and even more preferred to CA-XII.

Accordingly, in a preferred embodiment the antibody of the invention binds to carbonic anhydrase XII.

It is preferred in this regard that CA-XII is human CA-XII. It is furthermore preferred that the antibody binds to at least one epitope of the extracellular domain CA-XII (amino acids 25-301 of SEQ ID NO. 17), and even more preferred in the region of the discontinuous, catalytic domain of CA-XII (amino acids 94-199 of SEQ ID NO: 17 (Whittington et al. (2001). The term "extracellular domain" according to the present invention is a term well-known in the art and also relates in conjunction with the present invention to the portion of the CA-XII extending into the extracellular environment. Also the term "catalytic domain" according to the present invention is a term well-known in the art and also relates in conjunction with the present invention to the portion of the CA-XII at which catalysis of carbonic acid to bicarbonate and protons occurs.

As explained in more detail above, CA-XII is known for its role in hypoxia, cancer and eye disease and thus is an important target for diagnostic and medical purposes. The diagnostic and medical purposes of the instant invention are discussed in more detail herein below.

In a preferred embodiment the invention relates to an antibody comprising the $V_H$ region determined by the amino sequence of SEQ ID NO. 7 and the $V_L$ region determined by the amino sequence of SEQ ID NO. 8.

As stated herein above an antibody has two variable domains, the heavy chain domain $V_H$ and light chain domain $V_L$. SEQ ID NO. 7 and 8 show the sequence of the $V_H$ and $V_L$ domain of the antibody EXO 6A10 of the instant invention.

In a further preferred embodiment the antibody of the invention is a monoclonal antibody.

Monoclonal antibodies can be prepared, for example, by the well-established techniques as originally described in Kohler and Milstein, Nature 256 (1975), 495, and Galfre, Meth. Enzymol. 73 (1981), 3, which in this case comprise the fusion of mouse myeloma cells to spleen cells derived from immunized mammals with modifications developed by the art.

In this regard, it is of note that the antibody EXO 6A10 of the instant invention is a monoclonal antibody which has been raised in a rat to the human sequence of CA-XII as shown in FIG. 11 and encoded by the nucleic acid as shown in FIG. 12. Accordingly, it is particularly preferred that the monoclonal antibody of the invention is a rat monoclonal antibody.

In another preferred embodiment the antibody of the invention is coupled to (a) a labelling group, (b) a toxin, or (c) an anti-tumour drug.

In this regard the label group may be a hapten or a flurescent dye, for example selected from FLAG, GFP, YFP, RFP, dTomato, cherry, Cy3, Cy 5, Cy 5.5., Cy 7, DNP, AMCA, Biotin, Digoxigenin, Tamra, Texas Red, rhodamine, Alexa fluors, FITC, TRITC. Alternatively, the labelling group may be a radioisotopes such as for example $^3H$, $^{14}C$, $^{15}N$, $^{35}S$, $^{90}Y$, $^{99}Tc$, $^{111}In$, $^{125}I$, or $^{131}I$. Further examples of suitable labelling groups are enzymatic groups (e.g. horseradish peroxidase, horseradish galactosidase, luciferase, alkaline phosphatase), chemiluminescent groups, biotinyl groups, or predetermined polypeptide epitopes recognized by a secondary reporter (e.g. leucine zipper pair sequences, binding sites for secondary antibodies, metal binding domains, epitope tags).

The term "toxin" as used herein relates to any compound produced by living cells or organisms and poisonous to a cell or organism. A toxins, thus can be, e.g. small molecules, peptides, or proteins. Specific examples are neurotoxins, necrotoxins, hemotoxins and cytotoxins.

The term "anti-tumour drug" specifies in accordance with the invention a drug that is capable of either stopping or slowing down the abnormal growth of tissue. Thus anti-tumour drug are particularly useful in treating cancer. An anti-tumour drug may be a angiogenesis inhibitor, DNA intercalators or cross-linkers, DNA synthesis inhibitors, DNA-RNA transcription regulators, enzyme inhibitors, gene regulators, microtubule inhibitors or other antitumour agents.

It will be apparent to those skilled in the art that the antibodies of the invention can be coupled to a labelling group, a toxin, or an anti-tumour drug as defined herein above by methods well known in the art. Such coupling may be conducted chemically after expression of the antibody or antigen to the site of attachment or the coupling product may be engineered into the antibody or antigen of the invention at the DNA level. The DNAs are then expressed in a suitable host system as described herein below, and the expressed proteins are collected and renatured, if necessary. Coupling may be achieved via a linker known in the state of the art. In particular, different linkers that release the toxin, or an anti-tumour drug under acidic or reducing conditions or upon exposure to specific proteases may be employed with this technology.

In certain aspects, it may be desirable, that the labelling group, toxin, or an anti-tumour drug is attached by spacer arms of various lengths to reduce potential steric hindrance.

In a further embodiment the invention relates a nucleic acid molecule encoding the antibody according to the invention.

The nucleic acid molecule of the invention encoding the antibody of the invention may be, e.g. DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions required that the nucleic acid of the invention comprises nucleic acids encoding SEQ ID NOs 1 to 6 or SEQ ID NOs 7 and 8, or such sequences wherein at least one amino acid is conservatively substituted or comprises the nucleic acids as defined by SEQ NOs 9 to 15 or SEQ ID NOs 15 and 16.

In a particular preferred embodiment of the present invention, the nucleic acid molecule is a cDNA molecule.

An embodiment of the invention also relates to a vector comprising the nucleic acid molecule in an expressible form.

The vector of the invention may be, for example, a phage, plasmid, viral or retroviral vector. Retroviral vectors may be replication competent or replication defective. In the latter case, viral propagation generally will occur only in complementing host/cells.

The nucleic acid molecule may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRS-Vgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Plant expression vectors comprise pGEM-T (Promega), pCAMBIA 1391 (Cambia), GATEWAY (Invitrogen), pGreen and pGreenII (PGREEN). Examples for plasmid vectors suitable for Pichia pastoris comprise e.g. the plasmids pAO815, pPIC9K and pPIC3.5K (all Intvitrogen).

The nucleic acid molecule referred to above may also be inserted into vectors such that a translational fusion with another polynucleotide is generated. For vector modification techniques, see Sambrook and Russel (2001), loc. cit. Generally, vectors can contain one or more origin of replication (ori) and inheritance systems for cloning or expression, one or more markers for selection in the host, e. g., antibiotic resistance, and one or more expression cassettes. Suitable origins of replication (oil) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of transcription (e. g., translation initiation codon, promoters, such as naturally-associated or heterologous promoters and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers. Preferably, the polynucleotide of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Furthermore, it is preferred that the vector comprises a selectable marker. Examples of selectable markers include neomycin, ampicillin, and hygromycine, kanamycin resistance and the like.

An expression vector according to this invention is capable of directing the replication, and the expression, of the polynucleotide and encoded antibody of this invention. Suitable expression vectors which comprise the described regulatory elements are known in the art. In this regard, it is noted that $V_H$ and $V_L$ region of the antibody of the invention may be encoded by different expression vectors.

The nucleic acid molecules as described herein above may be designed for direct introduction or for introduction via liposomes, phage vectors or viral vectors (e.g. adenoviral, retroviral) into a host. Additionally, baculoviral systems or systems based on Vaccinia Virus or Semliki Forest Virus can be used as eukaryotic expression systems for the nucleic acid molecules of the invention.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropyl-β-thiogalactopyranosid ("IPTG"). For recombinant expression and secretion, the polynucleotide of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Alternatively, the recombinant polypeptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded polypeptide. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as

*E. coli, Streptomyces* and *Salmonella typhimurium* cells; fungal cells, such as yeast cells; insect cells such as *Drosophila* S2 and *Spodoptera* Sf9 cells; animal cells such as CHO, COS, HEK 293 and Bowes melanoma cells; and plant cells. Appropriate culture mediums and conditions for the above-described host cells are known in the art.

Another embodiment of the invention relates to a non-human host comprising the vector of the invention.

Said host may be a prokaryotic or eukaryotic cell. The polynucleotide or vector of the invention which is present in the host cell may either be integrated into the genome of the host cell or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

Suitable prokaryotic host cells comprise e.g. bacteria of the species *Escherichia, Bacillus, Streptomyces* and *Salmonella typhimurium*. Suitable eukaryotic host cells are e.g. fungal cells, inter alia, yeasts such as *Saccharomyces cerevisiae* or *Pichia pastoris* or insect cells such as *Drosophila* S2 and *Spodoptera* Sf9 cells and plant cells as well as mammalian cells. Appropriate culture media and conditions for the above-described host cells are known in the art. Mammalian host cells that could be used include, human Hela, HEK293, H9 and Jurkat cells, mouse NIH3T3 and C127 cells, Cos 1, Cos 7 and CV1, quail QC1-3 cells, mouse L cells, mouse C2C12 cells, BHK (baby hamster kidney cells) and Chinese hamster ovary (CHO) cells. Also within the scope of the present invention are hosts such as primary mammalian cells such as mouse embryonic fibroblasts (MEF). Alternatively, the recombinant antibody can be expressed in stable cell lines that contain the gene construct integrated into a chromosome. In a more preferred embodiment, said cell is a primary cell or primary cell line. Primary cells are cells which are directly obtained from an organism.

The invention also relates transgenic non-human animals comprising one or more nucleic acid molecules of the invention that may be used to produce the antibody of the invention. Antibodies can be produced in and recovered from tissue or body fluids, such as milk, blood or urine, of goats, cows, horses, pigs, rats, mice, rabbits, hamsters or other mammals. See, e. g., U.S. Pat. Nos. 5,827,690, 5,756,687, 5,750,172, and 5,741,957.

In a further embodiment the invention relates to a method for producing an antibody of the invention, comprising (a) culturing the host of the invention under conditions that allow synthesis of said antibody; and (b) recovering said antibody from said culture.

The transformed hosts can be grown in fermentors and cultured according to techniques known in the art to achieve optimal cell growth. Once expressed, the whole antibodies, of the present invention, can be purified according to standard procedures of the art, including ammonium sulfate precipitation, affinity columns, column chromatography, gel electrophoresis and the like; see, Scopes, "Protein Purification", Springer-Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention.

In another embodiment the invention relates to a diagnostic composition comprising the antibody of the invention, the nucleic acid molecule of the invention, the vector of the invention or the host of the invention.

The term "composition" as employed herein defines a composition comprising at least one antibody, nucleic acid molecule, vector, and/or host of the invention which are also referred in the following collectively as compound.

The diagnostic composition of the invention is useful in the detection of an undesired expression or over-expression of a CA, in particular CA-IX or CA-XII in different cells, tissues or another suitable sample, comprising contacting a sample with an antibody of the invention, and detecting the presence of a CA, in particular CA-IX or CA-XII in the sample. Accordingly, the diagnostic composition of the invention may be used for assessing the onset or the disease status as defined herein below. In particular, malignant cells, such as cancer cells expressing of a CA, in particular CA-IX or CA-XII, can be targeted with the antibody, antibody fragment or derivative thereof of the invention. The cells which have bound the antibody of the invention might thus be attacked by immune system functions such as the complement system or by cell-mediated cytotoxicity, therefore reducing in number of or eradicating cells showing undesired expression or over-expression of a CA, in particular CA-IX or CA-XII.

In one aspect of the present invention described herein above, the antibody, antibody fragment or derivative thereof of the invention is coupled to a labelling group. Such antibodies are particularly suitable for diagnostic applications.

The diagnostic composition of the invention can be administered as sole active agent or can be administered in combination with other agents.

In a further embodiment the invention relates to a pharmaceutical composition comprising the antibody of the invention, the nucleic acid molecule of the invention, the vector of the invention or the host of the invention.

The pharmaceutical composition is preferably administered to mammals such as domestic and pet animals. Most preferred it is administered to humans. The pharmaceutical compositions described herein can be administered to the subject at a suitable dose. The pharmaceutical composition for use in accordance with the present invention can be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. The pharmaceutical composition may, accordingly, be administered orally, parenterally, such as subcutaneously, intravenously, intramuscularly, intraperitoneally, intrathecally, transdermally, transmucosally, subdurally, locally or topically via iontopheresis, sublingually, by inhalation spray, aerosol or rectally and the like in dosage unit formulations optionally comprising conventional pharmaceutically acceptable excipients.

For oral administration, the pharmaceutical composition of the invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). The pharmaceutical composition can be administered with a physiologically acceptable carrier to a patient, as described herein. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts emulsifying agents, or pH buffering agents. These compositions can be in the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the aforementioned compounds, preferably in purified form, together with a suitable amount of carrier so as to provide the form for proper administration to the patient. The formulation should suit the mode of administration.

Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, sorbic acids). The preparations can also contain buffer salts, flavouring, colouring and sweetening agents as deemed appropriate. Preparations for oral administration can be suitably formulated to give controlled release of the pharmaceutical composition of the invention.

For administration by inhalation, the pharmaceutical composition of the invention is conveniently delivered in the form of an aerosol spray presentation from a pressurised pack or a nebulizer, with the use of a suitable propellant (e.g., dichlorodifluoromethane, trichlorofluoromethane, dichlorotetrafluoroethane, carbon dioxide or other suitable gas). In the case of a pressurised aerosol, the dosage unit can be determined by providing a valve to deliver a metered amount. Capsules and cartridges of, for example, gelatine, for use in an inhaler or insufflator can be formulated containing a powder mix of the pharmaceutical composition of the invention and a suitable powder base such as lactose or starch.

The pharmaceutical composition of the invention can be formulated for parenteral administration by injection, for example, by bolus injection or continuous infusion. Site of injections include intravenous, intraperitoneal or subcutaneous. Formulations for injection can be presented in units dosage form (e.g., in phial, in multi-dose container, sealed ampoules or vials, as an aqueous solution or as a lyophilized formulation for reconstitution), and with an added preservative. The pharmaceutical composition of the invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The pharmaceutical composition of the invention can be formulated for transdermal administration. Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention. The compounds of this invention can also be administered by a transdermal device. Accordingly, transdermal administration can be accomplished using a patch either of the reservoir or porous membrane type, or of a solid matrix variety.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The pharmaceutical composition of the invention can also, if desired, be presented in a pack, or dispenser device which can contain one or more unit dosage forms containing the said agent. The pack can for example comprise metal or plastic foil, such as blister pack. The pack or dispenser device can be accompanied with instruction for administration.

The pharmaceutical composition of the invention can be administered as sole active agent or can be administered in combination with other agents, preferably ones that are known in the art to be suitable for treatment of the disease in question.

The pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

According to an embodiment of the invention the antibody of the invention, the nucleic acid molecule of the invention, the vector of the invention or the host of the invention is for use in treating or inhibiting hypoxia, a solid tumor, or an eye disease.

Also described herein is a method for treating or inhibiting hypoxia, a solid tumor, or an eye disease by administering an effective amount of the nucleic acid molecule of the invention, the vector of the invention or the host of the invention to a subject in need thereof.

In this regard the term "hypoxia" refers to a pathological condition in which the body as a whole (generalized hypoxia) or a region of the body (tissue hypoxia) is deprived of adequate oxygen supply. For example, a mismatch between oxygen supply and its demand at the cellular level may result in a hypoxic condition. Hypoxia in which there is complete deprivation of oxygen supply is referred to as anoxia and therefore is embraced by the umbrella term hypoxia.

The term "solid tumour" in accordance with the invention defines an abnormal mass of tissue that usually does not contain cysts or liquid areas. Solid tumors may be benign (not cancer), or malignant (often referred to in the art as cancer). Different types of solid tumors are named for the type of cells that form them. Examples of solid tumors are provided herein below.

The term "eye disease" as used herein refers to a pathological condition or injury of the eye including its adnexa. An eye disease may for example involve the clouding or opacification of the natural lens of the eye, swelling of the macula for example resulting from leakage and accumulation of fluid or of the central retina, small accumulations of hyaline bodies underneath the retina, damages of the optic nerve, degeneration of the cells of the macula lutea, loss of vision or inflammation of the conjunctiva and cornea of the eye, and the formation of scar tissue. Examples of an eye disease are provided herein below.

As it will be appreciated by the person skilled in the art and as its is evident in particular from the information provided in the introductory part, which is incorporated by reference herein, the antibody, the nucleic acid molecule, the vector or the host of the invention are particularly useful in treating or inhibiting the particular diseases mentioned herein.

In a preferred embodiment of the invention the hypoxia is selected from tumor hypoxia, neuronal hypoxia, cerebral hypoxia, stenosis and ischemia.

In a further preferred embodiment of the invention the solid tumor is selected from sarcoma, glioma, carcinoma, mesothelioma, lymphoma, kidney tumor, lung tumor, mammary tumor, cervix tumor, ovarian tumor, colorectal tumor, liver tumor, prostate tumor, pancreas tumor and head and neck tumor.

In another preferred embodiment of the invention the eye disease is selected from ocular hypertension, glaucoma, macular degeneration, age-related macular degeneration, uveitis, retinitis, X-linked retinoschisis and hypertensive retinopathy.

The Figures show:

FIG. 1: Function of the carbonic anhydrases (taken from Innocenti et al., 2007). Interaction of cytosolic (CA-II) and transmenbrane (CA-IX and XII) with other proteins involved in PH homeostasis and anion transport such as (1) the monocarboxylate transporter. (2) the $Na^+$—$H^+$-antiporter; (3) the ATP-dependent $NA^+$—$K^+$-antiporters; (4) the $H^+$-ATP-ase; (5) acquaporins; (6) membrane-bound CAs (CA-IX, XII or XIV); (7) bicarbonate/chloride anion exchangers (AEs).

Figure 2:
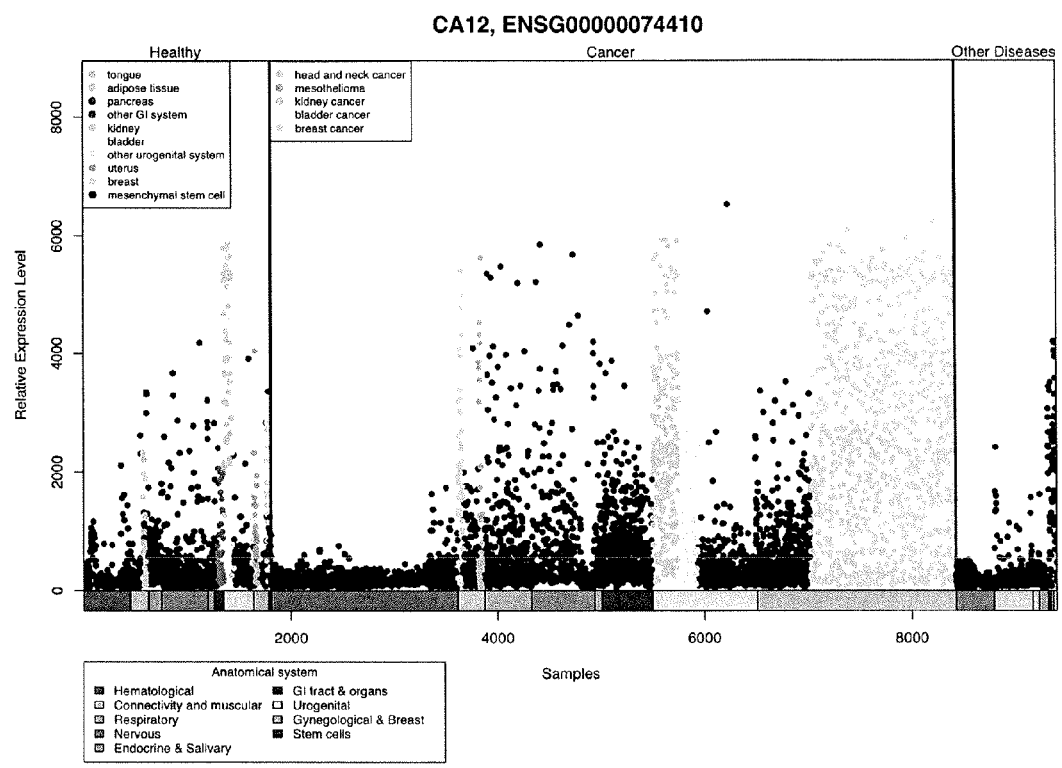

FIG. 2: CA-XII expression levels in different types of human cancer.

Figure 3:
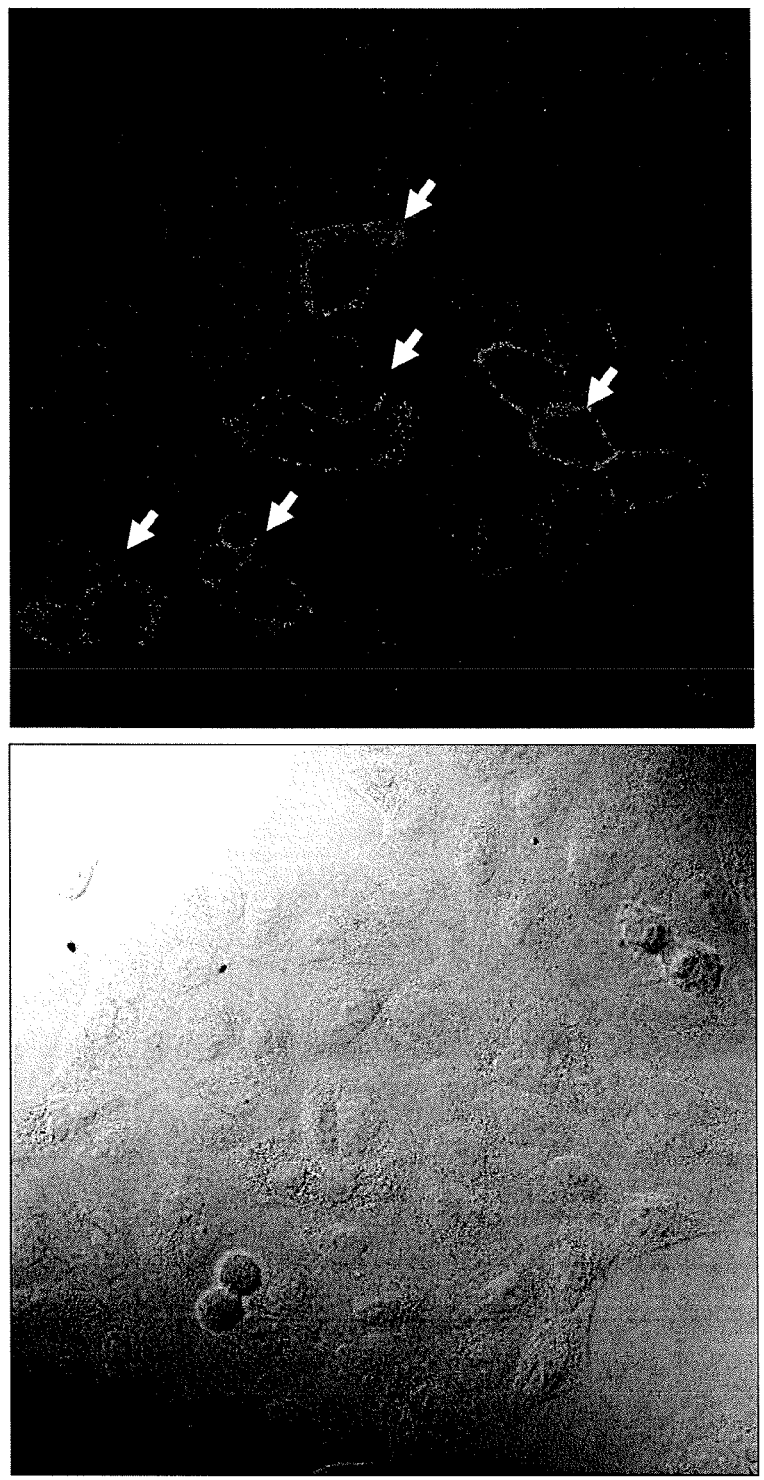

FIG. 3: Immunofluorecent staining of A549 cells with the antibody EXO 6A10 and a fluorochrome-labeled secondary antibody reveals the membrane-associated localization of CA-XII.

Figure 4:
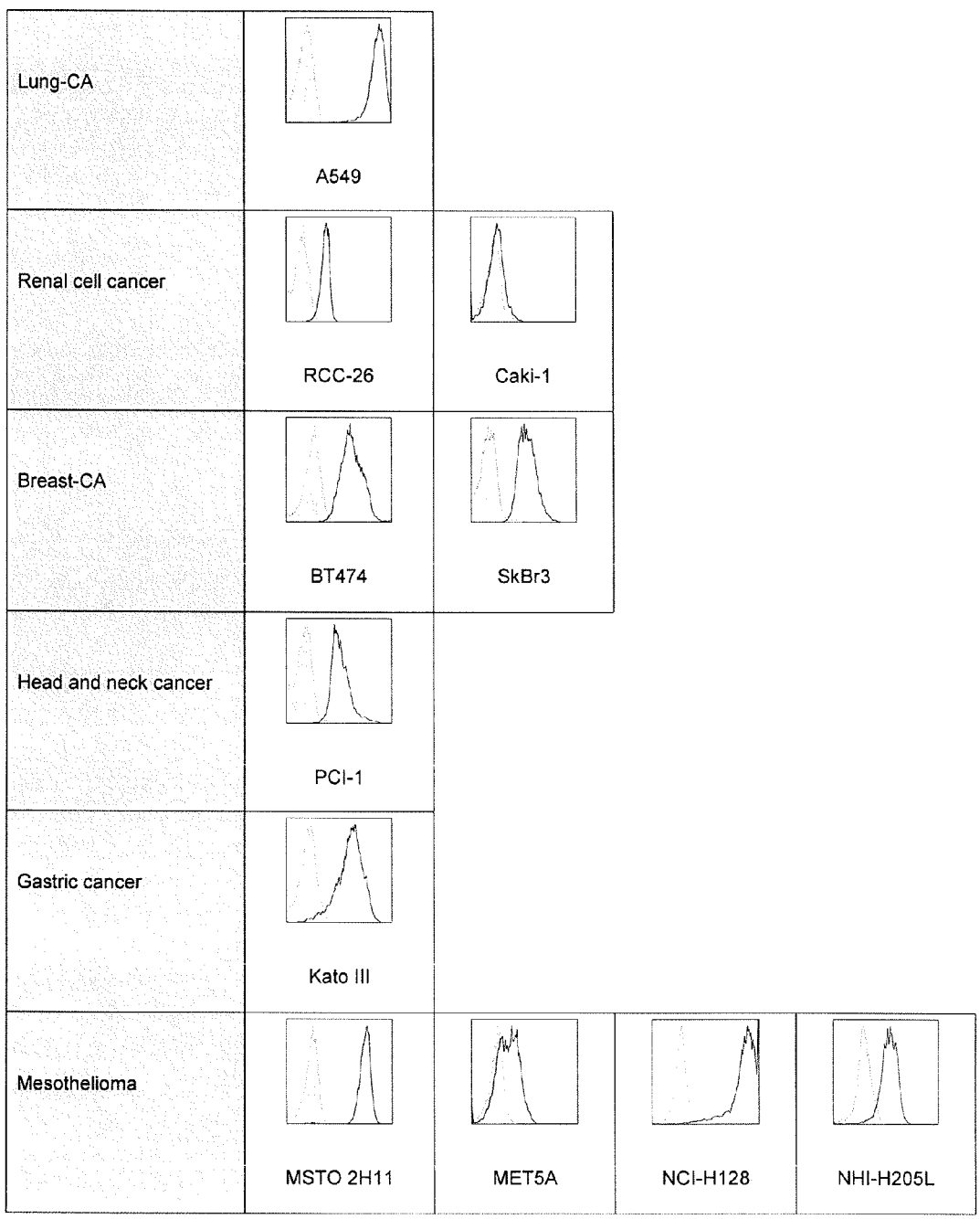

FIG. 4: A: CA-XII expression on the cell surface of human cancer cell lines and peripheral blood mononuclear cells (PBMC) as revealed by flow cytometry (grey are=isotype control; black line=EXO 6A10). B: CA-XII on exosomes isolated from the malignant ascites of a patient with ovarian cancer, as shown with immunoblot. GM1=ganglioside M1 (an exosomal marker); iso=isotype control.

FIG. 5: Top: EXO 6A10 inhibition of CA-XII (IC50=6.14× $10^{-9}$ M) and the sulfonamide azetazolamide (IC50=2.38× $10^{-7}$ M). Bottom: EXO 6A10 inhibition of CA II.

FIG. 6: Relevant amino acid residues of the discontinuous catalytic domain of CA-XII for the interference of EXO 6A10 with the activity of CA-XII. (taken from Whittington et al, 2001).

Figure 7:
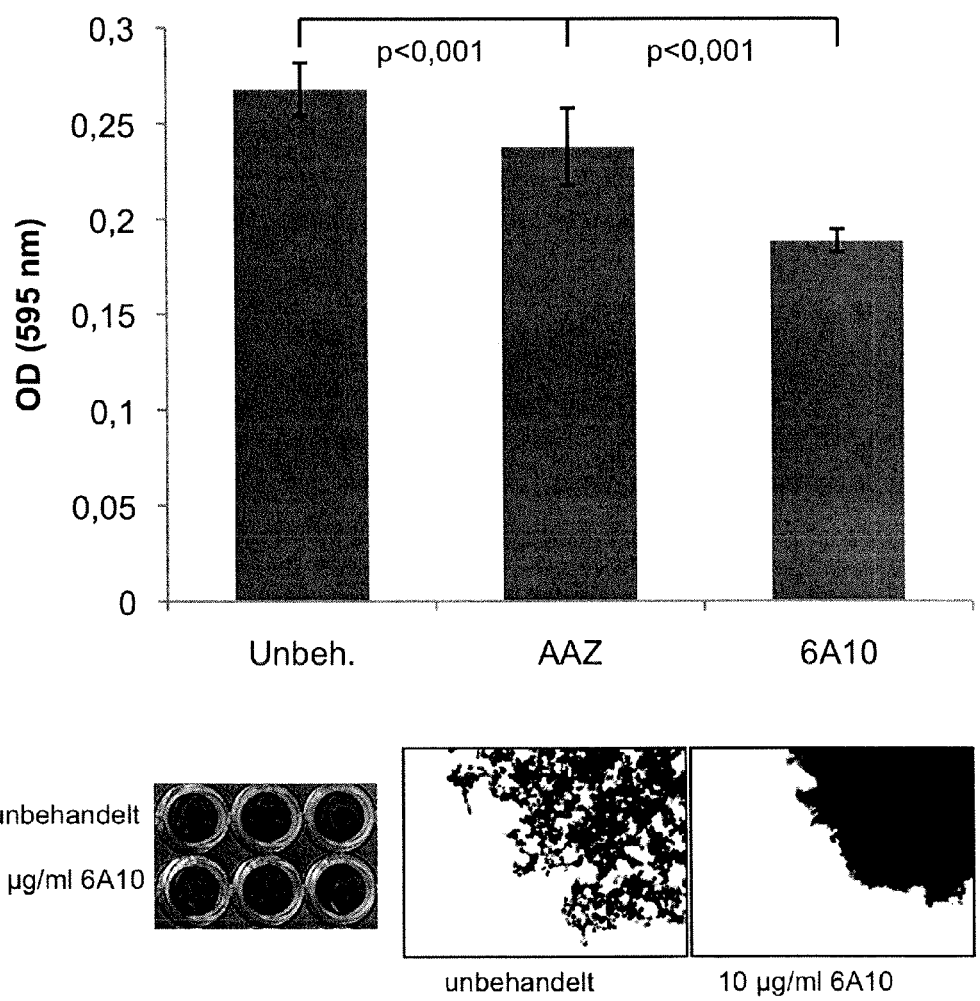

FIG. 7: EXO 6A10 inhibition of metabolic activity in 3-dimensional tumour spheroids. (Unbehandelt=non-treated) Upper: The spheroids were cultivated in the presence of EXO 6A10 (final concentration 10 µg/ml), with azetazolamide (AAZ, final concentration 100 µM) and control spheroids were cultivated without any additional treatment (Unbeh.). Metabolic acitivity of the spheroid was measured two days later by means of a MTT-assay and reading of the extinction at 595 nm (Cory et al. 1991). All data are represented as mean±standard error. Comparisons between non-treated and treated spheroids were performed using t-tests.

Lower: Pictures taken of A549 spheroids which were cultivated for two days with EXO 6A10 of left untreated and were subsequently treated with (3-(4,5-Dimethylthiazol-2-yl)-2,5-diphenhyltetrazoliumbromide.

FIG. 8: Nucleotide and amino acid sequences of the variable region of the immunoglobuline light chain of the hybridoma that produces the antibody EXO 6A10 (=6A10 hybridoma). The complemantary determining regions (CDRs) 1-3, constituting the interaction of the immunoglobulin with the antigen, are marked in yellow. CDRs were identified following criteria described in Chothia et al., 1989.

FIG. 9: Nucleotide and amino acid sequences of the variable region of the immunoglobuline heavy chain of the hybridoma that produces the antibody EXO 6A10 (=6A10 hybridoma). The complemantary determining regions (CDRs) 1-3, constituting the interaction of the immunoglobulin with the antigen, are marked in bold and underlined. CDRs were identified following criteria described in Chothia et al., 1989.

Figure 10:
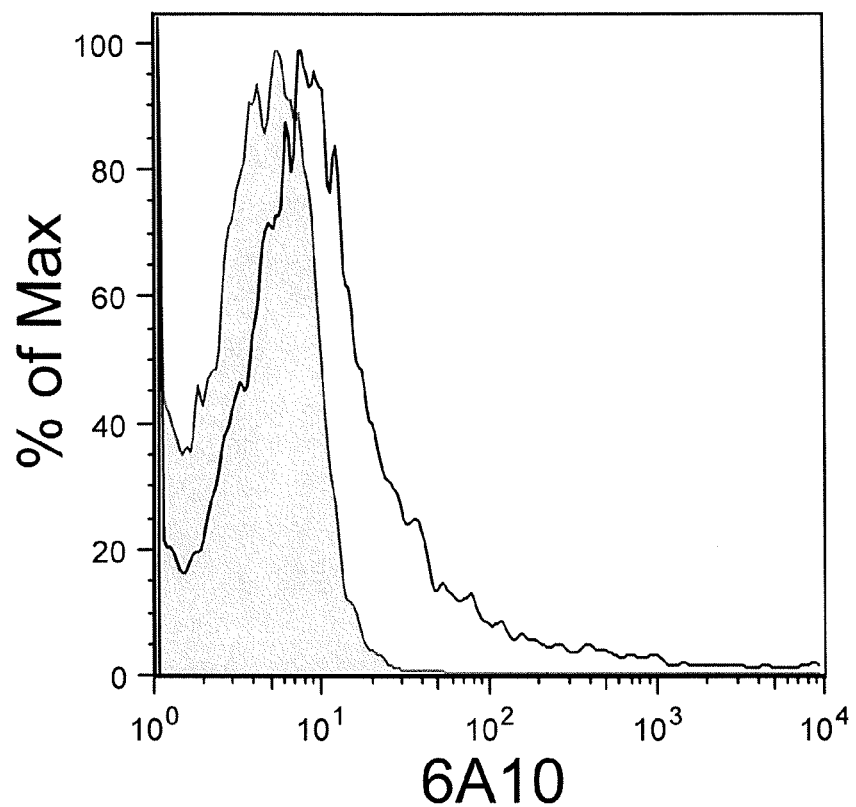

FIG. 10: Binding of EXO 6A10 in Murine L929 cells transfected with an expression plasmid encoding human CA-XII (black line, L929+CA-XII) and binding of EXO 6A10 to non-transfected L929-cells, as a control, (grey area, L929). revealed by flow cytometry.

FIG. 11: Alignment of the amino acid sequences of the published sequence of CA-XII, isoform 1 and the in silico translation of the cDNA that was cloned by RT-PCR. It is evident that both sequences are identical.

FIG. 12: Alignment of the published nucleotide acid sequences of CA-XII, isoform 1 and the cDNA that we cloned by RT-PCR. It is evident that both sequences are identical.

Figure 13:
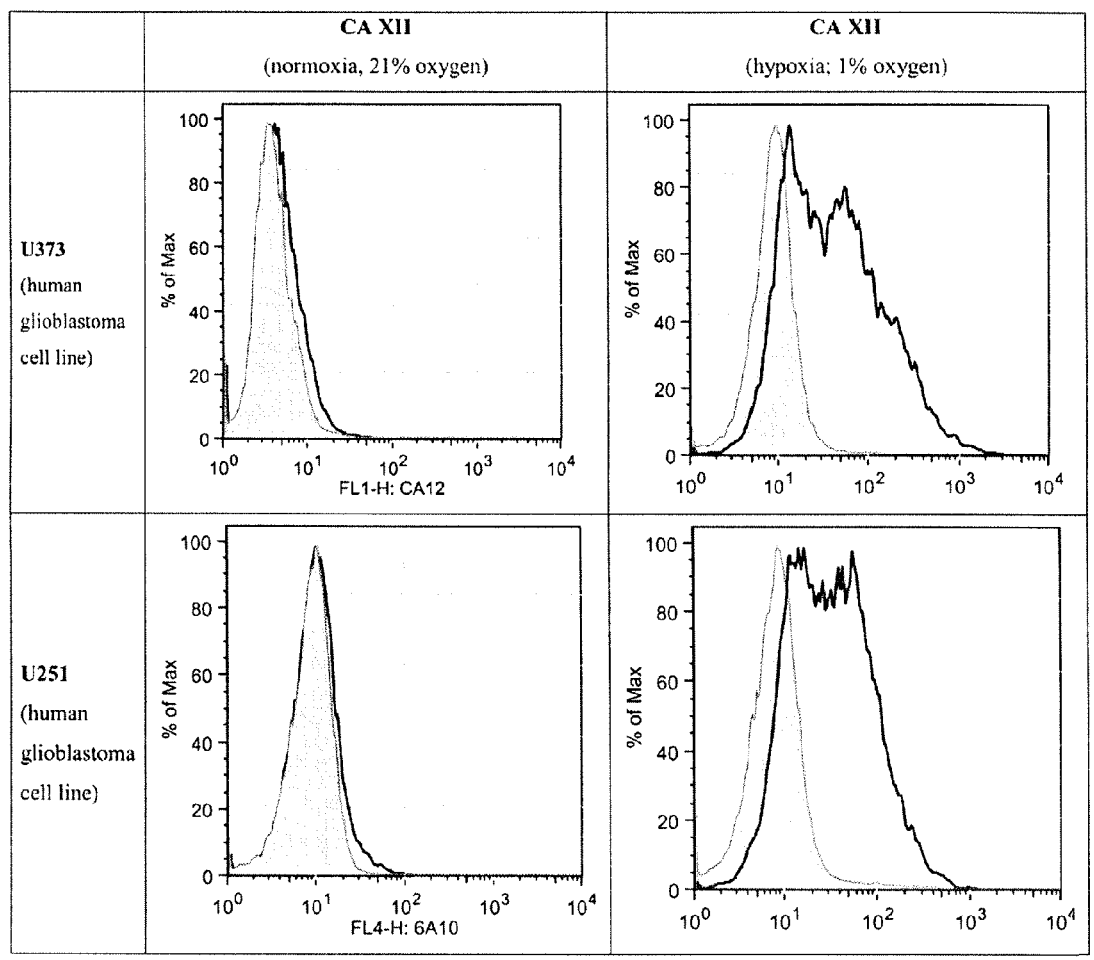

FIG. 13: Induction of CA XII expression on glioblastoma cell lines by hypoxia. Cells were cultivated either at 21% $O_2$ (normoxia) or at 1% $O_2$ (hypoxia) conditions. CAXII surface expression was measured by flow cytometry using the EXO 6A10 antibody. Black line=EXO 6A10, grey histogram=isotype control.

The Examples illustrate the invention.

EXAMPLE 1

CA-XII Expression Levels in Different Types of Human Cancer

CA-XII is highly expressed in different types of human cancer. Overexpression of CA XII is most evident on breast cancer, arguing for the data described in Bernett et al. (2008). (taken from: http://ist.genesapiens.org).

EXAMPLE 2

Immunofluorescent Staining of A549 Cells

A549 cells were fixed for 10 minutes with 4% (v/v) paraformaldehyde in PBS, washed with PBS and 0.5% (v/v) Triton-X-100 in PBS, and incubated with the EXO 6A10 antibody for 60 min at room temperature. After washing with PBS and PBS/0.5% (v/v) Triton-X-100, cells were incubated with a fluorochrome-labeled secondary antibody (mouse-anti-rat IgG/Cy3) and bound antibody was then visualized by a Leica laser-scanning microscope. Nuclei were counterstained with DAPI. As a result, staining of CA-XII is clearly associated with the cell membrane of A549 cells (FIG. 3, arrow heads).

EXAMPLE 3

Human Cancer Cell Lines Investigated Express CA-XII

Most permanent human cancer cell lines investigated express CA-XII on the cell surface as revealed by flow cytometry; cf. FIG. 4A. Permanent human cancer cell lines were incubated with EXO 6A10 (hybridoma supernatant diluted 1:5 in 2% (v/v) FCS (i.e., fetal calf serum) in PBS) for 15 min on ice, washed three times in PBS/2% (v/v) FCS and then stained with a specific secondary antibody (goat-anti-rat IgG/Cy5) for another 15 min on ice. Binding of 6A10 was then measured by flow cytometry in a Becton Dickinson FACS Calibur device and FlowJo software (Treestar Inc.). An antibody of the identical isotype with an irrelevant specificity (glutathione-S-transferase) was used as control. (grey are=isotype control; black line=EXO 6A10). No binding to peripheral blood mononuclear cells (PBMC) and to two melanoma cell lines (not shown) was detectable. FIG. 4B shows that CA-XII is also present on exosomes isolated from the malignant ascites of a patient with ovarian cancer, as shown with this immunoblot. Exosomes were isolated from malignant ascites by differential centrifugation (500×g; 10.000×g; 70.000×g) and resuspended in PBS. The protein concentration was measured in a standard Bradford assay. 2 µg protein were pipetted onto a nitrocellulose membrane. Membranes were incubated with the different primary antibodies. After washing, membranes were incubated with a specific secondary antibodiy (anti-rat IgG/peroxidase). Ganglioside GM1 was detected with cholera toxine subunit B/peroxidase. Membranes were developed with the ECL system.

EXAMPLE 4

CA-XII Inhibition by EXO 6A10 and Azetazolamide

EXO 6A10 inhibits CA-XII (IC50=$6.14 \times 10^{-9}$ M) much more efficiently as compared to the sulfonamide azetazolamide (IC50=$2.38 \times 10^{-7}$ M); cf. FIG. 5, Top. In contrast, EXO 6A10 does not significantly inhibit CA-II; cf. FIG. 5, Bottom.

EXAMPLE 5

EXO 6A10 Binding to CA-XII

Three-dimensional structure of the catalytic domain of CA XII. Shown are relevant amino acid residues (taken from Whittington et al, 2001).

EXAMPLE 6

EXO 6A10 Inhibition of Metabolic Activity in 3-Dimensional Tumour Spheroids

A549 lung cancer cells were plated onto a cushion consisting of 1% (v/v) agarose in PBS on a 96-well cell culture plate. Under these conditions, most cell lines that grow as monolayer in standard cell culture, do not adhere to agarose. Instead cells spontaneously form 3-dimensional structures termed tumour spheroids.

FIG. 7, Upper: Some of the spheroids were cultivated in the presence of EXO 6A10 (final concentration 10 µg/ml) whereas others were cultivated with acetazolamide (AAZ, final concentration 100 µM). Control spheroids were cultivated without any additional treatment (Unbeh.). The metabolic acitivity of the spheroid was measured two days later by means of a MTT-assay as described and reading of the extinction at 595 nm (Cory et al. 1991). For each group, 10 spheroids were included, the mean value, the standard deviation were calculated. All data are represented as mean±standard error. Comparisons between non-treated and treated spheroids were performed using t-tests, calculated using Prism4 (GraphPad Software, La Jolla).

FIG. 7, Lower: A549 spheroids were cultivated for two days with EXO 6A10 or left untreated. Then, (3-(4,5-Dimethylthiazol-2-yl)-2,5-diphenyltetrazoliumbromide was added and pictures were taken. It is obvious that EXO 6A10-treated spheroids are much smaller and much more dense than untreated spheroids.

EXAMPLE 7

Transfection of Murine L929 Cells with an Expression Plasmid Encoding Human CA-XII Murine L929 cells were transfected with an expression plasmid encoding human CA-XII. Binding of EXO 6A10 was then revealed by flow cytometry (FIG. 10, black line, L929+CA-XII). As a control, binding of EXO 6A10 to non-transfected L929-cells was tested (FIG. 10, grey area, L929). EXO 6A10 binds to transfected but not to non-transfected cells. As a result, indicating the binding of membrane localized overexpressed human CA-XII.

EXAMPLE 8

Culturing of Glioblastoma Cell Lines U373 and U251 Under Normoxia or Hypoxic Conditions CA XII is associated with hypoxia in human cancer. Glioblastoma cell lines U373 and U251 were cultured either at normoxia (approx. 21% $O_2$) or under hypoxic conditions (1% $O_2$). Whereas CA XII was not detectably expressed under normoxic conditions (left histograms) the enzyme was clearly induced when cells were kept under hypoxia (FIG. 13). These results implicate that CA XII is an important enzyme for hypoxic cancer cells.

References

Alterio, V., Hilvo, M., Di Fiore, A., Supuran, C. T., Pan, P., Parkkila, S., Scaloni, A., Pastorek, J., Pastorekova, S., Pedone, C., Scozzafava, A., Monti, S. M., and De Simone, G. (2009). Crystal structure of the catalytic domain of the tumor-associated human carbonic anhydrase IX. Proc Natl Acad Sci USA 106, 16233-16238.

Barnett, D. H., Sheng, S., Charn, T. H., Waheed, A., Sly, W. S., Lin, C. Y., Liu, E. T., and Katzenellenbogen, B. S. (2008). Estrogen receptor regulation of carbonic anhydrase XII through a distal enhancer in breast cancer. Cancer Res 68, 3505-3515.

Chiche, J., Ilc, K., Laferriere, J., Trottier, E., Dayan, F., Mazure, N. M., Brahimi-Horn, M. C., and Pouyssegur, J. (2009). Hypoxia-inducible carbonic anhydrase IX and XII promote tumor cell growth by counteracting acidosis through the regulation of the intracellular pH. Cancer Res 69, 358-368.

Chothia, C., Lesk, A. M., Tramontano, A., Levitt, M., Smith-Gill, S. J., Air, G., Sheriff, S., Padlan, E. A., Davies, D., Tulip, W. R., and et, a. (1989). Conformations of immunoglobulin hypervariable regions. Nature 342, 877-883.

Cory, A. H., Owen, T. C., Barltrop, J. A., and Cory, J. G. (1991). Use of an aqueous soluble tetrazolium/formazan assay for cell growth assays in culture. Cancer Commun 3, 207-212.

Innocenti, A., Vullo, D., Pastorek, J., Scozzafava, A., Pastorekova, S., Nishimori, I., and Supuran, C. T. (2007). Carbonic anhydrase inhibitors. Inhibition of transmembrane isozymes XII (cancer-associated) and XIV with anions. Bioorg Med Chem Lett 17, 1532-1537.

Kivela, A., Parkkila, S., Saarnio, J., Karttunen, T. J., Kivela, J., Parkkila, A. K., Waheed, A., Sly, W. S., Grubb, J. H., Shah, G., Tureci, O., and Rajaniemi, H. (2000). Expression of a novel transmembrane carbonic anhydrase isozyme XII in normal human gut and colorectal tumors. Am J Pathol 156, 577-584.

Thiry, A., Supuran, C. T., Masereel, B., and Dogne, J. M. (2008). Recent developments of carbonic anhydrase inhibitors as potential anticancer drugs. J Med Chem 51, 3051-3056.

Ulmasov, B., Waheed, A., Shah, G. N., Grubb, J. H., Sly, W. S., Tu, C., and Silverman, D. N. (2000). Purification and kinetic analysis of recombinant CA XII, a membrane carbonic anhydrase overexpressed in certain cancers. Proc Natl Acad Sci USA 97, 14212-14217.

Vullo, D., Innocenti, A., Nishimori, I., Pastorek, J., Scozzafava, A., Pastorekova, S., and Supuran, C. T. (2005). Carbonic anhydrase inhibitors. Inhibition of the transmembrane isozyme XII with sulfonamides—a new target for the design of antitumor and antiglaucoma drugs? Bioorg Med Chem Lett 15, 963-969.

Whittington, D. A., Waheed, A., Ulmasov, B., Shah, G. N., Grubb, J. H., Sly, W. S., and Christianson, D. W. (2001). Crystal structure of the dimeric extracellular domain of human carbonic anhydrase XII, a bitopic membrane protein overexpressed in certain cancer tumor cells. Proc Natl Acad Sci USA 98, 9545-9550.

The invention claimed is:

1. An antibody binding to a carbonic anhydrase, wherein the antibody comprises:
the amino acid sequences SEQ ID NOS: 1 (CDR 1), 2 (CDR 2) and 3 (CDR 3) determining the CDRs of the $V_H$ region, and the amino acid sequences SEQ ID NOS: 4 (CDR 1), 5 (CDR 2) and 6 (CDR 3) determining the CDRs of the $V_L$ region.

2. The antibody of claim 1, which binds to carbonic anhydrase XII.

3. The antibody of claim 1, wherein said antibody comprises the $V_H$ region determined by the amino sequence of SEQ ID NO. 7 and the $V_L$ region determined by the amino sequence of SEQ ID NO. 8.

4. The antibody of claim 1, wherein said antibody is a monoclonal antibody.

5. The antibody according of claim 1, wherein said antibody is coupled to (a) a labelling group,
(b) a toxin, or
(c) an anti-tumor drug.

6. A nucleic acid molecule encoding the antibody of claim 3.

7. A vector comprising the nucleic acid molecule of claim 6 in an expressible form.

8. A non-human host comprising the vector of claim 7, wherein the non-human host is a prokaryotic cell or a eukaryotic cell.

9. A method for producing the antibody of claim 1, comprising the steps of:
(a) culturing a non-human host, wherein the non-human host is a prokaryotic cell or a eukaryotic cell, under conditions that allow synthesis of said antibody; and
(b) recovering said antibody from said culture.

10. A diagnostic composition comprising the antibody of claim 1.

11. A pharmaceutical composition comprising the antibody of claim 1.

12. The pharmaceutical composition of claim 11, for use in treating or inhibiting hypoxia, a solid tumor, ocular hypertension, glaucoma, or hypertensive retinopathy.

13. The pharmaceutical composition of claim 12, wherein said hypoxia is selected from tumor hypoxia, neuronal hypoxia, cerebral hypoxia, stenosis and ischemia.

14. The pharmaceutical composition of claim 12, wherein the solid tumor is selected from the group consisting of: sarcomas, glioma, carcinoma, mesotheliom, lymphoma, kidney tumor, lung tumor, mammary tumor, cervix tumor, ovarian tumor, colorectal tumor, liver tumor, prostate tumor, pancreas tumor and head and neck tumor.

15. The antibody of claim 1, wherein the antibody binds to at least one epitope of the extracellular domain of carbonic anhydrase 12, wherein said extracellular domain comprises amino acids 25-301 of SEQ ID NO: 17.

16. The antibody of claim 15, wherein the antibody binds to at least one epitope of the discontinuous, catalytic domain of carbonic anhydrase 12, wherein said discontinuous, catalytic domain comprises amino acids 94-199 of SEQ ID NO: 17.

17. A nucleic acid molecule encoding the antibody of claim 1.

18. The nucleic acid molecule of claim 17, wherein the nucleic acid molecule is a cDNA.

\* \* \* \* \*